(12) United States Patent
Franzmann et al.

(10) Patent No.: US 12,128,178 B2
(45) Date of Patent: Oct. 29, 2024

(54) INHALERS AS WELL AS PROTECTIVE DEVICE AND BREATH INDICATOR

(71) Applicant: BOEHRINGER INGELHEIM VETMEDICA GMBH, Ingelheim am Rhein (DE)

(72) Inventors: Benjamin Franzmann, Merxheim (DE); Peter Bauer, Irmelshausen (DE); Guido Endert, Leichlingen (DE); Johannes Krieger, Mellrichstadt (DE); Marcus Rainer Rahmel, Ockenheim (DE); Jonas Ruf, Cologne (DE); Horst Wergen, Essen (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 880 days.

(21) Appl. No.: 15/734,744

(22) PCT Filed: May 20, 2020

(86) PCT No.: PCT/EP2020/064050
§ 371 (c)(1),
(2) Date: Dec. 3, 2020

(87) PCT Pub. No.: WO2020/239569
PCT Pub. Date: Dec. 3, 2020

(65) Prior Publication Data
US 2021/0330904 A1    Oct. 28, 2021

(30) Foreign Application Priority Data

May 24, 2019  (WO) ............. PCT/EP2019/063473

(51) Int. Cl.
*A61M 15/00*    (2006.01)
*A61M 15/08*    (2006.01)

(52) U.S. Cl.
CPC ...... *A61M 15/0071* (2014.02); *A61M 15/009* (2013.01); *A61M 15/08* (2013.01); *A61M 2205/27* (2013.01)

(58) Field of Classification Search
CPC ............ A61M 15/0071; A61M 15/009; A61M 15/08; A61M 2205/27
See application file for complete search history.

(56) References Cited

U.S. PATENT DOCUMENTS

| 5,666,948 | A  | 9/1997  | Matson          |
|-----------|----|---------|-----------------|
| 5,833,088 | A  | 11/1998 | Kladders et al. |
| 7,806,295 | B2 | 10/2010 | Stradella et al.|
| 8,430,271 | B2 | 4/2013  | Poulard         |

(Continued)

FOREIGN PATENT DOCUMENTS

| CN | 207356334 U | 5/2018 |
|----|-------------|--------|
| CN | 102671273 A | 9/2019 |

(Continued)

*Primary Examiner* — Steven O Douglas
(74) *Attorney, Agent, or Firm* — Calderon Safran & Wright P.C.; David S. Safran

(57) ABSTRACT

An inhaler with a protective device for protecting the inhaler against removal or replacement of the cartridge, having a readiness indicator for displaying a not-ready-to-trigger state or a ready-to-trigger state, and a breath indicator. Also, an inhaler with an insert for putting the inhaler into a ready-to-trigger state and/or for breaking a tamper-proof seal.

23 Claims, 12 Drawing Sheets

(56) References Cited

U.S. PATENT DOCUMENTS

| | | | |
|---|---|---|---|
| 8,950,393 | B2 | 2/2015 | Holakovsky et al. |
| 9,713,516 | B2 | 7/2017 | Knell et al. |
| 9,724,482 | B2 | 8/2017 | Bach et al. |
| 9,913,952 | B2 | 3/2018 | Knell et al. |
| 10,046,124 | B2 | 8/2018 | Knell et al. |
| 2008/0173301 | A1 | 7/2008 | Deaton et al. |
| 2009/0229609 | A1 | 9/2009 | Carrier |
| 2012/0279498 | A1 | 11/2012 | Nakamura |
| 2012/0304991 | A1 | 12/2012 | Gotliboym et al. |
| 2013/0206136 | A1 | 8/2013 | Herrmann et al. |
| 2015/0053203 | A1 | 2/2015 | Knell et al. |
| 2017/0281886 | A1 | 10/2017 | Knell et al. |

FOREIGN PATENT DOCUMENTS

| | | |
|---|---|---|
| SU | 1127598 A1 | 12/1984 |
| WO | 2015024653 A1 | 2/2015 |

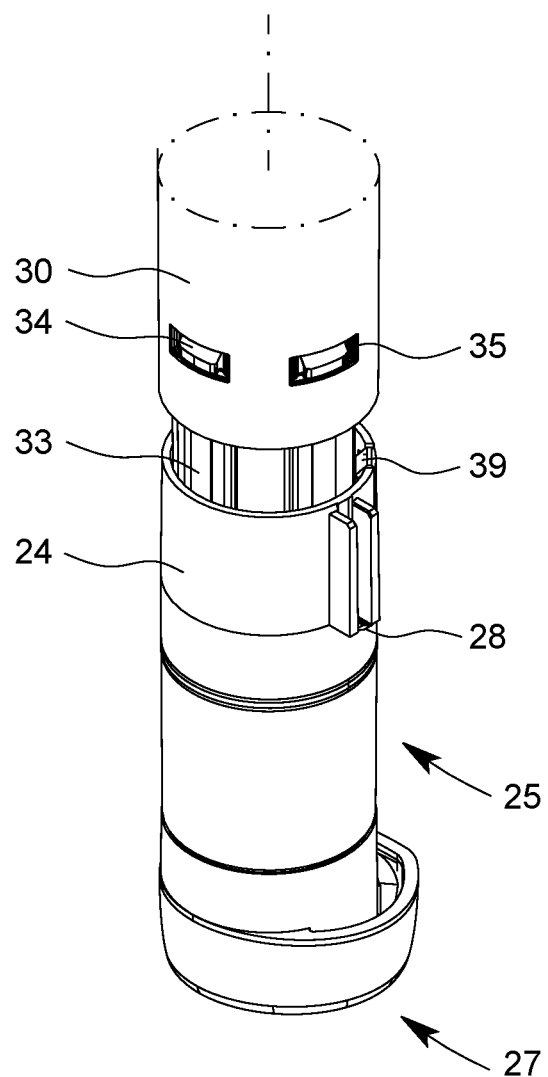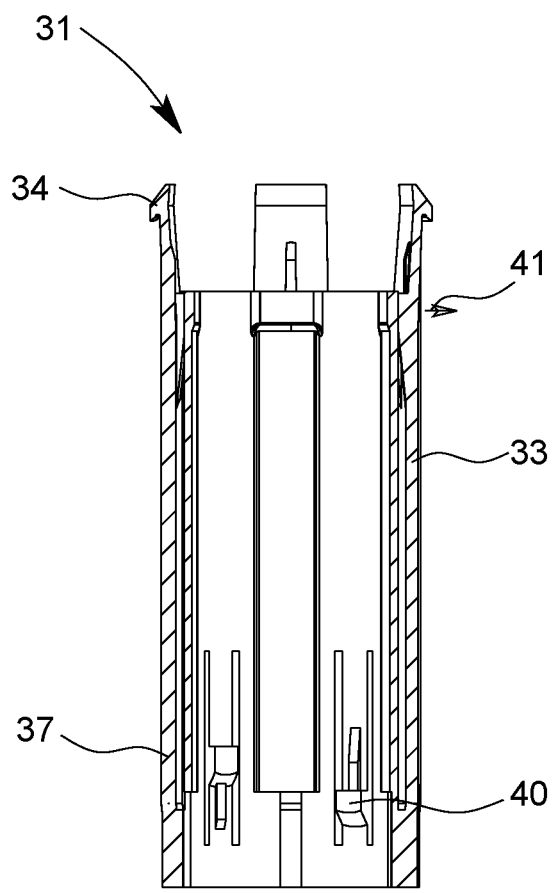
Fig. 5
Fig. 6

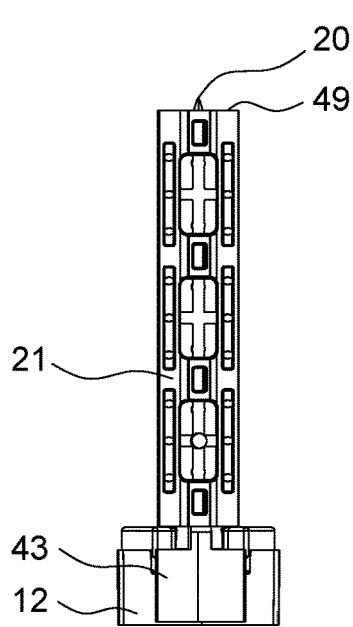
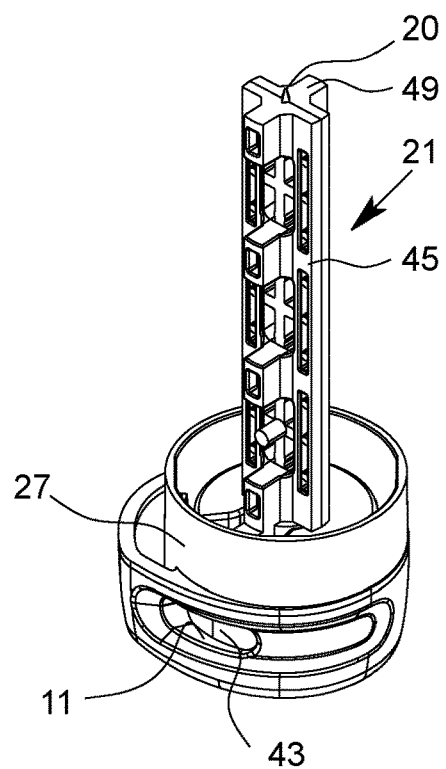
Fig. 12    Fig. 13
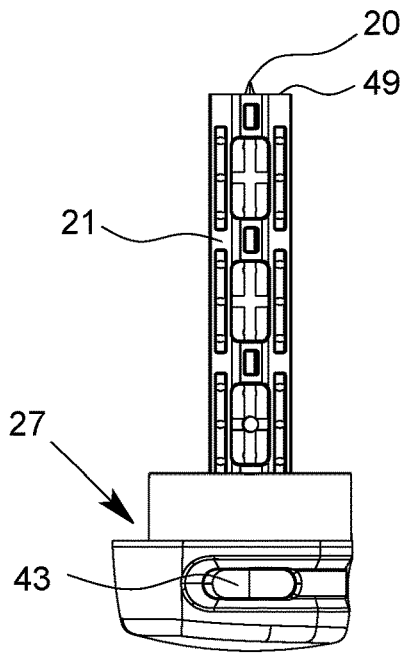
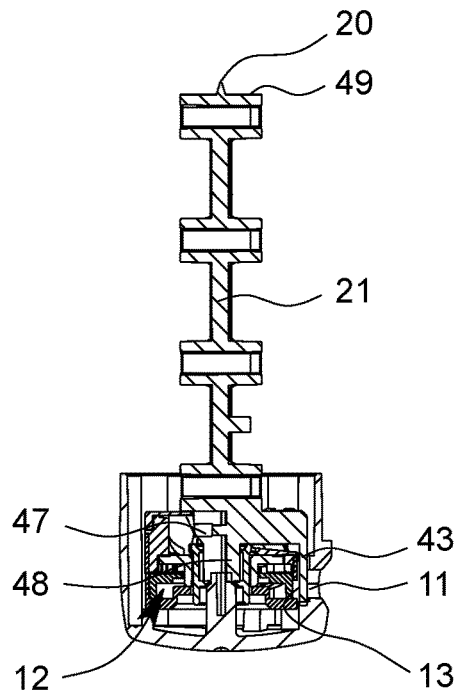
Fig. 14    Fig. 15

INHALERS AS WELL AS PROTECTIVE DEVICE AND BREATH INDICATOR

BACKGROUND OF THE INVENTION

Field of the Invention

This invention relates to the field of inhalers. In particular, this invention relates to inhalers for use in the veterinary medicine sector, preferably with an adapter for a respiratory opening of a body, in particular for insertion into a nostril, for example a horse's nostril. This invention is not limited to this field, however.

Description of Related Art

Inhalers of the kind in question are designed for dispensing, in particular by spraying or atomizing, a medication. These are preferably inhalers for therapeutic purposes, in particular for forming a respirable aerosol from a medication in the form of a liquid or a powder, which is contained or can be contained in a cartridge of the inhaler and can be dispensed by the inhaler.

This invention relates, moreover, preferably to so-called Soft Mist Inhalers (SMI), i.e., inhalers that produce an atomized spray (aerosol) that propagates only comparatively slowly. In terms of this invention, such inhalers are in particular inhalers in which an aerosol is dispensed at a speed of less than 2 m/s, preferably approximately 1.6 m/s or less, and quite especially preferably less than 1 m/s (in each case measured at a distance of 10 cm from a discharge nozzle) and/or in which the dispensing or spraying of a dose—of preferably 10 to 50 µl of a pharmaceutical agent preparation—lasts longer than 0.7 s, in particular approximately 1 s or longer. This invention is especially advantageous in connection herewith, but is not limited thereto.

Inhalers of the kind in question are known in principle, for example, from International Patent Application Publication WO 2015/024652 A1 corresponding to U.S. Pat. No. 9,713,516 B2, International Patent Application Publication WO 2015/024650 A1 corresponding to U.S. Pat. No. 10,046,124 B2, International Patent Application Publication WO 2015/024651 A1 corresponding to U.S. Pat. No. 9,913,952 B2, and International Patent Application Publication WO 2015/024653 A1, the entire contents of which are incorporated herein by reference and to which in addition reference is made in particular with respect to the basic functions of the inhaler.

SUMMARY OF THE INVENTION

In accordance with a first aspect, this invention relates to an inhaler for dispensing a medication, wherein the inhaler has a cartridge for the medication that is received in a housing of the inhaler.

In the case of inhalers of the kind in question, observance of hygiene standards is partially hampered in such a way that such inhalers are used in the veterinary medicine sector and in part in stables, whereby even in the case of regular cleaning, contamination of surfaces cannot be ruled out. Moreover, the correct metering represents a challenge in particular because of a possibly adverse environment and a specific active ingredient concentration in the medication.

Thus, when using inhalers for treatment of larger animals such as horses or camels, etc., it is useful to use active ingredient concentrations and/or dosages that deviate from human-medicine inhalers and vice versa.

In order to reduce improper handling and thus the risk of a mis-dosage, it is provided in the case of inhalers of the kind in question that the cartridge for the medication is not to be removed or replaced. This limits, moreover, the period of use of the inhaler. In this way, infections are prevented.

It has turned out, however, that the only instruction concerning this matter is to some extent not followed, whereby mis-dosages and infections can occur in a corresponding manner.

An object of the first aspect of this invention is therefore to provide an inhaler for administering a medication and a protective device, whereby application safety is improved.

This object is achieved by an inhaler and a protective device as described herein.

According to the first aspect of this invention, it is provided that the inhaler has a protective device for protecting the inhaler before removal and/or replacement of the cartridge for the medication that is received in the housing of the inhaler.

The inhaler is designed by means of the protective device to be damaged when the inhaler is tampered with for the purpose of removing or replacing the cartridge, so that the inhaler becomes unusable for the dispensing of the medication unless the protective device is repaired or replaced.

In other words, by this protective device, the inhaler is designed in such a way that the cartridge is removable from the housing only in the event of damage or destruction by which the inhaler is unusable for dispensing the medication.

The protective device is thus a device of the inhaler that is specifically designed to be damaged or destroyed when the inhaler is tampered with for the purpose of removing and/or replacing the cartridge. This is achieved in particular in such a way that the protective device has scoring points or tear points and/or other structural measures at which the protective device is damaged or destroyed when tampered with for the purpose of removing and/or replacing the cartridge before access to the cartridge or the removal and/or replacement of the latter is possible.

Because of the structurally-caused damage or destruction of the protective device, further (proper) use of the inhaler is prevented. Advantageously, in this way, a mis-dosage by replacing the cartridge can be prevented and/or infections can be avoided, since the inhaler is unusable after the protective device is damaged and destroyed, and accordingly cannot be used longer than intended anymore. As a result, in the veterinary medicine sector, this is thus conducive to animal protection.

Especially preferably, the protective device holds the cartridge in the inhaler and/or parts of the inhaler together. For example, it can be provided that the protective device is designed to cease holding the cartridge in the inhaler or the parts of the inhaler together in the event there is destruction. Consequently, use of the inhaler, and in particular a fastening of the cartridge and/or an operation of the inhaler for dispensing the medication, is prevented.

Accordingly, the protective device is preferably designed in such a way that when the inhaler is tampered with for the purpose of removing or replacing the cartridge, the function of holding the cartridge, or of holding the parts of the inhaler together, is lost. In this way, it can be prevented that the inhaler can be used further for dispensing the medication.

In an especially preferred embodiment, the protective device has one or more fastening device(s). The fastening device(s) can hold the cartridge in the inhaler and/or parts of the inhaler together.

In this case, it is preferred that the inhaler be designed in such a way that the fastening device(s) are damaged when tampered with for the purpose of removing or replacing the cartridge. In this way, the function to hold the cartridge in the inhaler, or the parts of the inhaler together, can be lost. As an alternative or in addition, in this way, the dispensing of the medication can be prevented.

The fastening device(s) extend(s) preferably on a side facing away from the cartridge along a longitudinal axis of the protective device. In this way, a separating action exerted on the housing of the inhaler, in particular in the area or for the purpose of removing or replacing the cartridge, will automatically lead to damage or destruction, by which the protective device loses the function of holding the cartridge in the inhaler and/or the parts of the inhaler together.

Preferably, the at least one fastening device has an arm, which carries a latching element for a latching hold of the protective device, wherein by separating the arm or by damage to the latching element, the protective device loses the function of holding the cartridge in the inhaler and/or the parts of the inhaler together.

Also in this connection, it is preferred that the protective device be designed specifically in such a way that when tampered with for the purpose of removing or replacing the cartridge, damage in the area of the arm and/or the latching element takes place automatically, so that the tampering results in destruction before the cartridge is accessible.

For example, the cartridge can be received in a resting position in the protective device, so that in the attempt to gain access to the cartridge through the housing wall of the inhaler, damage to the fastening system(s) is caused. The protective device is preferably designed specifically to provoke such damage.

As an alternative or in addition, the protective device can form an insert, a slide-in guide that is designed as a complement thereto, or a part of the insert and/or the slide-in guide, wherein the inhaler is shifted or can be shifted to a ready-to-use state by inserting the insert or moving the insert relative to the slide-in guide.

In particular, this can be an insert that shifts the cartridge into a position of use and/or prepares the inhaler and/or the cartridge for the purpose of removing the medication that is contained in the cartridge.

Moreover, it is preferably further provided that the insert for administering the medication has to be held in an inserted position (in the inhaler), which is achieved or can be achieved with the protective device. The protective device is preferably designed and/or provided in the inhaler in such a way that when the inhaler is tampered with for the purpose of removing or replacing the cartridge, it provokes damage of the protective device, so that the insert is no longer held in its inserted position in the inhaler. In this way, a subsequent dispensing of the medication can be prevented.

In particular, the protective device or the inhaler with the latter is designed in such a way as to cease holding the insert in the inserted position in the event there is damage to the fastening device(s), in which position it must be held, however, for the inhaler to be or remain suitable for dispensing the medication.

In particular, in this way, it can be achieved that after the cartridge is replaced, a protective device that is damaged or destroyed by corresponding tampering ensures that the insert or parts of the insert is or are pulled out from the inhaler upon actuation of the latter, instead of triggering taking place or a trigger readiness being reached.

In a preferred further development, the insert and/or the slide-in guide is/are made in multiple parts, and the parts of the insert and/or the slide-in guide is/are connected to one another by the fastening device(s) of the protective device, so that in the event of damage to the fastening device(s), in particular, thus, when an arm is severed or damage is done to a latching means of the fastening device, the insert and/or the slide-in guide or a part thereof become movable, whereby the preparation of the triggering and/or a dispensing of the medication is subsequently prevented.

The fastening devices or arms preferably extend over a vast majority of the length of the protective device and/or over a length that exceeds the length of the cartridge. In particular, it is thus provided that the fastening device(s) extend(s) directly or at a distance along the cartridge. In this case, the fastening device(s) can preferably project over the cartridge.

At a distance along the cartridge preferably means that a projection of the cartridge transversely to its longitudinal axis at least essentially overlaps with the fastening device(s).

In this way, it can be achieved that tampering with the housing of the inhaler from the side, i.e., in particular the attempt to saw the housing for the purpose of removing or replacing the cartridge, results in severing one or more of the fastening device(s). This thus represents a preferred measure, by which the protective device is designed, when the inhaler is tampered with for the purpose of removing or replacing the cartridge, to provoke the damage or destruction of the protective device. The damage or destruction in turn has the effect, as already previously described, that the inhaler is rendered unusable for a further dispensing of the medication (without repairing or replacing the protective device).

The protective device preferably further has a receiving device for the cartridge. The receiving device is preferably sleeve-like. The receiving device can be designed so as to receive and/or embrace the cartridge. The cartridge can be held and/or mounted inside the receiving device and/or can be movable. Here, however, other approaches are also possible.

On one end, the receiving device preferably has a fastening region, to which the fastening device(s) is/are connected to the receptacle. The fastening device(s) is or are preferably formed as an integral piece with the receptacle, in particular injection-molded.

Starting from the fastening region, the (respective) arm of the fastening device(s) runs and/or extends parallel to a longitudinal axis or center axis of the receiving device.

The longitudinal axis or center axis in this case preferably corresponds to an axis of symmetry of the receiving device and/or axis of symmetry of the cartridge that is received or receivable in the receiving device or vice versa.

The arm runs preferably starting from the fastening region up to a free end of the (respective) fastening device(s)/of the (respective) arm along the receiving device, wherein the (respective) latching element is arranged at the (respective) free end of the fastening device(s)/of the (respective) arm. Furthermore, the arm is preferably free-standing and/or is not held or fastened (on the receiving device) between the fastening region and the latching element.

The protective device, in particular receptacle, preferably receives the cartridge or encloses it. The protective device, in particular receptacle, can form a guide for the cartridge, so that the cartridge is movably mounted, in particular axially, within the protective device or receptacle. The protective device or receptacle can have at least one stop for the cartridge, which limits an especially axial movement of the cartridge in the protective device.

The receptacle is preferably formed by a sleeve, which has an at least essentially cylindrical and/or tubular cavity. This cavity corresponds to the shape of the cartridge preferably in such a way that the cartridge is held securely in the receptacle and/or is guided to move along the cavity inside the receptacle. To this end, the cartridge preferably has an at least essentially cylindrical basic shape with an outside diameter that falls below the inside diameter of the receptacle to the extent that the cartridge is received or receivable with clearance in the receptacle.

By means of the stop, the protective device can be designed to effect that the inhaler is unusable for further dispensing of doses of the medication in the event of damage or destruction. This is explained in more detail below:

The inhaler is preferably designed to move or to clamp the cartridge against the stop, in particular for preparing a trigger readiness and/or for triggering and/or in another phase of operation of the inhaler for the purpose of dispensing the medication with the latter.

Moving or clamping the cartridge against the stop can be a function-essential part of the process for dispensing the medication that can be or is contained in the cartridge or in principle can first be carried out independently thereof.

In this case, it is preferred that the protective device be moved or be movable relative to another part of the insert or the slide-in guide, after being damaged to the fastening device(s), due to the parts of the insert and/or the slide-in guide being no longer—or no longer adequately—connected, so that the dispensing of the medication is prevented directly or indirectly.

In particular, by the damage to the protective device, it can be achieved that in the attempt to actuate the inhaler subsequently for the purpose of dispensing the medication, the protective device or a part of the inhaler held by the protective device and/or insert and/or slide-in guide, optionally including the cartridge, is automatically ejected or at least shifted. In this way, a defect can be signaled visibly from the outside, and a triggering of the inhaler can be prevented.

As a result, the protective device can exert its protective action in the immediate environment of the cartridge, in such a way that when the inhaler is tampered with for the purpose of removing or replacing the cartridge, damage and/or destruction of the protective device is caused or provoked by the design of the protective device, and in this way, the inhaler then is not serviceable anymore, cannot be put into a ready-to-use state, and/or the inhaler simply cannot be used anymore.

Another, also independently achievable aspect of this invention relates to the protective device for the inhaler, which is designed for protection of the inhaler against removal and/or replacement of the cartridge, so that the cartridge can be removed from the housing only upon damage or destruction, whereby the inhaler is rendered unusable for dispensing the medication.

The protective device preferably has the features that have already been described previously in connection with the inhaler and that are specific to the protective device.

In particular, it is provided that the protective device has one or more fastening device(s), which have arms running along the protective device, on which end-side latching elements are formed.

The protective device is preferably provided with a sleeve-like receptacle, in which the cartridge can be received.

Furthermore, it is preferred that the protective device has the stop for limiting the movement of the cartridge in the receptacle.

Altogether, in the protective device, it is thus preferred that the stop is formed in the receptacle, and the arms are fastened to one end of the receptacle, on which also the stop is provided, and at which the fastening device(s) are connected to the receptacle in a fastening region.

The fastening device(s) can consequently extend along the receptacle at the level of the cartridge. The cartridge can receive force from the cartridge by the stop opposite to the course of the fastening device(s) starting from the fastening region along the direction of the receptacle to the latching means and/or can exert tensile loading on the fastening device(s) upon clamping the cartridge against the stop.

This ensures that a shifting of the protective device with or without cartridge can be used especially easily and effectively to prevent further operability of the inhaler after the protective device is damaged and/or destroyed.

In another aspect of this invention, an inhaler, which optionally can implement one or more of the previously-explained features, has a not-ready-to-trigger state and a ready-to-trigger state.

This means that for triggering, the inhaler first must be shifted from the not-ready-to-trigger state to the ready-to-trigger state in order to be subsequently triggerable, preferably before and/or for the purpose of each triggering and/or dispensing of a dose of the medication.

It has been shown that the use of the inhaler is more comfortable and safer when the ready-to-trigger state or not-ready-to-trigger state can be recognized.

In the second aspect of this invention, an object of this invention is therefore to provide an inhaler for dispensing a medication that is more comfortable to operate and/or in which application safety is improved.

This object is achieved by an inhaler as described herein.

To achieve this object, it is provided that the inhaler has a readiness indicator to display the ready-to-trigger state and/or the not-ready-to-trigger state.

The readiness indicator is quite especially preferably an optical indicator or a variable optical display, which triggers different optical impressions depending on the ready-to-trigger state or not-ready-to-trigger state.

The inhaler preferably has an energy storage for driving a preferably mechanical pump. The energy storage can in particular be a spring, but can also be implemented differently.

In this case, the energy storage or the pump is designed for delivering medication with the inhaler. To this end, the medication can be delivered, in particular nebulized, by means of the energy storage or the pump. In particular, the pump that is driven by the energy storage can to this end convey the medication from the cartridge to a nozzle, which then nebulizes the medication.

In the case of a powder inhaler, it can be provided that the energy storage drives a preferably mechanical pump for pumping air, which provides air pressure for nebulizing the powder of the powder inhaler.

The putting of the inhaler into the ready-to-trigger state can in this case take place by adding energy to the energy storage, in particular thus, by tensioning the spring. In this way, energy is available to drive the pump. Accordingly, a delivery of the medication can be done by subsequent triggering.

Also, alternative or additional other measures can be provided, however, to put an inhaler into a ready-to-trigger state, in particular also without adding energy to an energy storage. The latter is especially preferred, however.

The inhaler is preferably put, starting from the not-ready-to-trigger state, into the ready-to-trigger state preferably before each triggering for the purpose of dispensing a dose of the medication. In this case, this is a preferably obligatory and causal change of state for each individual dispensing of the medication.

By putting the inhaler into the ready-to-trigger state, a preferably optical displaying is carried out by the readiness indicator. This optical displaying thus depends thereon and signals the difference between the ready-to-trigger state and the not-ready-to-trigger state.

In a preferred aspect of this invention, the readiness indicator produces the optical displaying by a movement that is caused upon putting the inhaler into the ready-to-trigger state.

In particular, when adding energy to the energy storage for the purpose of subsequent activation, a movement of the readiness indicator takes place by which the optical display is produced.

The readiness indicator especially preferably changes or conceals a display (which is independent of the readiness indicator and/or which is another display) of the inhaler and thus indicates the state or is designed for this.

The readiness indicator is preferably designed to display the difference between the not-ready-to-trigger state and the ready-to-trigger state by the change in the extent to which a display of the inhaler is concealed.

The inhaler preferably has a dose indicator for displaying the doses of a medication that have been or can still be dispensed with the inhaler, which dose indicator is at least partially concealed by the readiness indicator at least in one of the states. In the other of the states, a concealment is accordingly not provided or provided to a different degree, so that the degree of the concealment displays the state.

In principle, the same housing window can be shared by the readiness indicator and another indicator of the inhaler, in particular the dose indicator.

In this connection, the dose indicator can be visible through the housing window of the inhaler, and the readiness indicator can use the same housing window for display of the state.

Also here, it is preferred that the readiness indicator share the window with the dose indicator in that the readiness indicator at least partially conceals the dose indicator in one of the states, and in the other of the states, at least essentially unblocks the view to the dose indicator.

In general, it is thus preferred that the readiness indicator and dose indicator share a window in the housing of the inhaler and/or another display. In this way, an especially transparent and accordingly simple and reliable operation of the inhaler can be made possible.

The readiness indicator can be coupled to a part of the inhaler that is located in different positions depending on the ready-to-trigger state or not-ready-to-trigger state, in particular to a cartridge, an actuating lever, a pump piston, an energy storage, in particular a spring end, or the like.

It can be provided that the readiness indicator is coupled to a drive of the dose indicator, so that the dose indicator is actuated and/or driven when the readiness indicator displays the change in state and/or is moved.

In this connection, it can thus also be provided that the readiness indicator conceals a view of the dose indicator upon putting the inhaler into the ready-to-trigger state, and simultaneously actuates the dose indicator. As an alternative or in addition, it can be provided that the readiness indicator unblocks a view of the dose indicator and simultaneously actuates the dose indicator upon putting the inhaler into the ready-to-trigger state.

The readiness indicator can be or have a covering element such as a curtain, which upon a change in state—partially or completely opens or closes the window in the housing of the inhaler before the display of the dose indicator, so that the display of the dose indicator is concealed or can be seen from outside.

Another, also independently achievable, third aspect of this invention that can advantageously be combined with the preceding and subsequent aspects relates to a breath indicator for display of a respiratory action in the case of an inhaler, wherein the breath indicator is designed for airtight closure of an indicator opening of an adapter, communicating with a respiratory opening, of the inhaler for a respiratory opening.

In this connection, it has been shown that a display of the respiratory action that is as pronounced and/or that can be clearly interpreted as possible is desirable.

An object of this invention in the third aspect is therefore to indicate an inhaler for dispensing a medication, in which the display action of the breath indicator is improved.

This object is achieved by a breath indicator as described herein.

The breath indicator has a flexible membrane for display of a pressure differential between opposite flat sides of the membrane, whereby the pressure differential can be generated by the respiratory action. In particular, it is thus provided that inhalation or exhalation through an animal's respiratory opening into the or from the adapter results in a pressure differential on the membrane because of the fact that the adapter communicates with the indicator opening. The pressure differential deforms and/or moves the membrane inward and/or outward, by which the respiratory action is indicated or can be indicated.

According to this aspect, the membrane has at least two half-waves at least in one direction (in cross-section) and/or is at least essentially untensioned and/or wavy at least in one direction.

It has been shown, surprisingly enough, that in this way, even in the case of very low pressure differentials, a deflection and/or deformation of the membrane can be achieved, which makes possible or promotes a clearer visualization of the respiratory action.

It is thus preferred that depending on the respiratory action, the membrane is deflected to a greater extent, since in this way, a more differentiated and more exact evaluation of the respiratory phase can be carried out. Consequently, an inhaler that is assigned to the breath indicator can be triggered at the correct time or in a synchronized manner, so that a medication can be administered more reliably with the inhaler.

In this aspect, this invention thus leads to an improved application safety and to an improved operating comfort of an inhaler assigned to the breath indicator.

Especially preferably, in cross-section, the membrane has two beads that are formed by half-waves. These beads can be produced separately from one another or can be formed in an interconnecting manner.

In principle, a circumferential bead is thus possible, which bead separates an inside region, surrounded by this bead, from an edge region of the membrane, at which edge region the membrane can be connected or connectable in an airtight manner to the indicator opening.

Preferred, however, are at least two beads that run separately from one another and further preferably run at least essentially parallel to one another. Surprisingly enough, the latter result in that especially reflections of the breath indicator—when viewed from the side and when the membrane is deflected under respiratory action—are highly variable and thus make the phase of respiratory action especially easy to recognize.

The beads can have a material thickness that is less than the material thickness of the regions of the membrane that surround it. As an alternative or in addition, the flexibility of the membrane in the area of the beads can be increased by avoiding material tensioning and/or by material excess by creating a fold. This is conducive to an improved display of the respiratory action.

In a special embodiment, the half-waves or beads are designed as wave troughs, which (directly) limit a wave peak formed between the beads. As a result, the membrane is wavy as a whole; i.e., in the cross-section, it has a course in which (at least) one wave trough is followed by (at least) one wave peak, and in particular, in turn is followed by a wave trough.

The amplitude of the wave peak preferably arranged in the center can, in this regard, be larger than the amplitude of the wave troughs that limit the wave peak. This applies in particular relative to an imaginary zero line, which is formed by a surface that corresponds to a membrane tensioned across the indicator opening in all directions by a connecting line, the connecting line continuing a wall of a chamber surrounding the breath indicator and/or the connecting line being of fastening and/or support points of the membrane being straight in a cross sectional view.

In this way, the wave peak rises and drops upon respiratory action, while the wave troughs or beads support this by their flexibility and/or depending on the respiratory action change or reverse their direction of curvature (from concave to convex and vice versa), which leads to an especially characteristic visibility of phases of the respiratory action.

It can be provided that the breath indicator is injection-molded, preferably wherein the injection point is provided between the beads or in the area of the wave peak.

Furthermore, it is preferred that the membrane in one direction be at least essentially unwaved and/or tensioned and/or curved. In particular, it can be provided that the membrane in one direction has the at least two half-waves, is untensioned and/or wavy, while the membrane in another direction, preferably running transversely or perpendicular to this, does not have this (these) property(ies). The waves, half-waves, and/or beads preferably have an amplitude of more than 0.5 mm, preferably more than 1 mm, and/or more than 10 times the material thickness of the membrane in the area of waves, half-waves, and/or beads, in particular in the resting position without differential pressures in the membrane, which preferably applies accordingly for other explanations.

In another aspect of this invention, which can also be carried out independently and can advantageously be combined with the preceding and subsequent aspects, an inhaler has the described breath indicator, wherein the breath indicator for display of a respiratory action closes an indicator opening of the inhaler in an airtight manner, which communicates with an adapter for a respiratory opening, so that a pressure differential that is produced by the respiratory action can be displayed with the breath indicator.

Another, also independently achievable, fourth aspect of this invention, which can also be produced independently and can be combined with the preceding and subsequent aspects, relates to an inhaler with a cartridge, with or for receiving a medication, which is, in a delivery state, secured in a housing against removal from the housing or is pre-inserted into a housing of the inhaler, wherein when using the inhaler, the medication can be dispensed by the latter. In this connection, it has been shown that as easy and comfortable a preparation of the inhaler as possible for subsequent use is desirable.

An object of this invention is in the fourth aspect, therefore, to provide an inhaler for administering a medication, which can be easily put into a ready-to-use state.

This object is achieved by an inhaler as described herein.

According to the fourth aspect of this invention, the inhaler has an insert and preferably an especially complementary slide-in guide that corresponds thereto. The inhaler can be put in a ready-to-use state by inserting the insert into the housing. As an alternative or in addition, a tamper-proof seal is broken automatically by inserting the insert.

The use of the insert has, surprisingly enough, turned out to be especially feasible. In particular, in the case of inhalers for the veterinary medicine sector, in this case it is advantageous that with the insert, also with gloves as are used in the stable, the inhaler can be put in the ready-to-use state or operated simply and hygienically.

Preferably, the cartridge can be prepared for removing the medication inside the housing by inserting the insert.

In the delivery state of the inhaler, the insert preferably projects from the housing, in particular from a grip or housing-grip part, of the inhaler and can be manually inserted at least partially into the housing.

In the delivery state of the inhaler, the cartridge preferably is in a position and/or a state in which no medication can be removed from the cartridge for the purpose of dispensing by the inhaler. In particular, the cartridge is sealed in the delivery state. The cartridge can be opened and/or connected by putting into the ready-to-use state, so that subsequently, medication can be removed from the cartridge and dispensed by the inhaler. Especially preferably, the latter is achieved with or by the insert, by inserting the insert into the housing.

A first latching position or pre-latching position can be provided, in which the insert projects from the housing into the delivery state of the inhaler, but is held in a non-detachable manner.

Preferably, a (second) latching position is provided, upon reaching of which the insert engages irreversibly in an inserted position. In this way, the insert is held in an inserted position. It is not ruled out that the insert starting from the (second) latching position can be moved still further in the insert direction and back to the (second) latching position but not beyond that anymore, in particular back into the first latching position.

It can be provided that, also in the (second) latching position and/or in the ready-to-use state, the insert projects from the housing (a little). The projection of the insert beyond the housing is, however, permanently lower in the (second) latching position in comparison to the delivery state of the inhaler.

By inserting the insert, the cartridge preferably goes into a receptacle for the cartridge, which is provided inside the housing of the inhaler. In this way, the cartridge can be held in a latching manner in a position of use, in which medication can be removed from the cartridge and can be dispensed by the inhaler.

By inserting the insert, the cartridge is, as an alternative or in addition, opened, unlocked, or tapped, by which a removal of the medication that is contained or can be contained in the cartridge and/or an aeration of the cartridge is made possible.

The insert preferably has a dose indicator. As an alternative or in addition, the insert has a readiness indicator to display a trigger readiness.

The insert preferably has a pin, on which the readiness indicator and/or an actuating section for actuating the dose indicator is/are provided. The pin can be moved in the insert. In particular, the pin is mounted in the insert in such a way that it is guided linearly and/or is secured against rotating. The pin is preferably elongated and/or made cross-shaped in section transverse to its longitudinal extension. Here, however, other approaches are also possible.

In the case of the inhaler, the pre-inserted cartridge has the advantage that dosage uncertainties due to incorrect insertion of the cartridge and/or due to insertion of an incorrect cartridge are avoided. The specific production based on the insert, which can be shifted relative to the slide-in guide in the housing of the inhaler, in this case makes possible an especially easy and reliable putting of the inhaler in the ready-to-use state. At the same time, the insert makes it possible to store the cartridge in the housing of the inhaler (in the delivery state of the inhaler) in a completely sealed state, which enhances storage life.

An inhaler, in terms of the present invention, is preferably a device for dispensing a preferably liquid or powdery medication. In particular, this is a device for nebulizing the medication and/or for forming an aerosol with the medication.

A medication, in terms of the present invention, is a preferably liquid or powdery substance, which has an active ingredient. In this case, the active ingredient is preferably pharmacologically active.

A protective device, in terms of the present invention, is a structural element or a structural measure of the inhaler, which is designed and/or constructed specifically to provoke damage when the inhaler is tampered with for the purpose of removing and/or replacing the cartridge.

In this case, the protective device provides protection before the cartridge is removed and/or replaced and/or before the inhaler is used for dispensing the medication after such tampering. At least indirectly, the protective device accordingly preferably provides protection against a misdosage by using unsuitable medications in replaced cartridges and/or against infections due to an unintendedly long use of the inhaler, which could be made possible without the protective device by replacing the cartridge.

A fastening device, in terms of the present invention, is a device that is used in the fastening and/or is suitable for fastening.

A separating action, in terms of the present invention, is in particular a cutting, sawing or the like. A separating action on the housing is thus in particular a cutting or sawing open of the housing.

An arm, in terms of the present invention, is an elongated structure, i.e., has a length that exceeds the diameter by a multiple. As an alternative or in addition, an arm, in terms of the present invention, is fastened only on one end, and is unfastened or open on the second end that faces away from the fastened end. This relates to the arm as such, which does not rule out that the arm on the open end can be designed for fastening to another part, in particular by a latching element.

A latching element, in terms of the present invention, is a structure that is designed and equipped in such a way as to engage in a positive manner in a complementary structure. In particular, in this case, this is a hook, an undercut, or the like.

The latching element is preferably designed for irreversible positive fastening and/or holding. The latching element thus preferably forms a non-detachable connection with the complementary structure. In this connection, a non-detachable connection is defined in that the connection, which is produced with the or by means of the latching element, can be detached only when a part of the inhaler, in particular the protective device, is damaged or destroyed.

A ready-to-use state in terms of the present invention is a state in which the inhaler is prepared for dispensing the medication. In contrast to this, a state that is not ready-to-use is such a state, in particular a storage or delivery state, starting at which the inhaler must first be prepared before the medication can be dispensed. An insert in terms of the present invention is a device such as a drawer, a slide or the like, which is movably mounted on or in the inhaler, and can be pushed further into the housing of the inhaler.

A slide-in guide in terms of the present invention is a structure that corresponds to the insert or that is formed in a complementary manner, which makes possible, in particular guides, the inserting of the insert into the housing of the inhaler.

Sleeve-like in terms of the present invention is a structure that is tubular at least partially or in sections.

A receiving device in terms of the present invention is a structure that bounds an interior space that is shaped for receiving—preferably the cartridge. A ready-to-trigger state in terms of the present invention is a state of the inhaler that makes possible a direct triggering of the administering of the medication. In particular, a ready-to-trigger state is characterized in that in the ready-to-trigger state, an energy storage is loaded or a mainspring for a pump is pretensioned.

A not-ready-to-trigger state in terms of the present invention is a state of the inhaler, starting from which the inhaler must first be prepared, in particular by adding energy to an energy storage and/or tensioning a mainspring in order to be ready to trigger and/or to be put into the ready-to-trigger state.

Both in the ready-to-trigger state and in the not-ready-to-trigger state, in terms of the present invention, the inhaler is preferably ready to use. The cartridge is thus preferably opened and/or connected, so that in principle, the medication can be removed and dispensed.

Preferably, the inhaler according to the proposal is first to be put from the not-ready-to-trigger state into the ready-to-trigger state for each individual dispensing of a dose of the medication. By triggering and/or dispensing the dose of the medication, the inhaler leaves the ready-to-trigger state again and returns to the not-ready-to-trigger state. A trigger cycle of the inhaler for dispensing a dose of the medication thus preferably comprises exactly one change in state from the not-ready-to-trigger state into the ready-to-trigger state, and a second change in state from the ready-to-trigger state into the not-ready-to-trigger state.

Preferably, the inhaler in question always necessarily has to be put between two triggerings from the not-ready-to-trigger state, which is reached by triggering and/or dispensing the medication, first into the ready-to-trigger state, so that a next triggering and/or dispensing of the medication can be carried out.

A dose indicator in terms of the present invention is a device for displaying doses that have been dispensed or can still be dispensed with the inhaler. In other words, the dose indicator is suitable for displaying how much of the medication contained in the cartridge has already been dispensed or can still be dispensed. The term "dose indicator", in terms of the present invention, is preferably to be understood broadly and comprises both counters to display doses that are dispensed or can still be dispensed exactly or numerically, as well as indicators that provide a rough indication only in percentage or in another way of how much medication or how many doses have been dispensed or can still be dispensed—also called fill level indicator or fill level display. The dose indicator thus preferably has a display that provides an indication for the fill level of the cartridge with the medication, in particular without giving an exact or numerical indication of doses that have been dispensed or can still be dispensed.

A breath indicator in terms of the present invention is a device for displaying a state or a phase within a respiratory process of a living creature. In particular, the breath indicator makes it possible to displaying inhalation activity and/or exhalation activity. The breath indicator preferably displays the respiratory action optically. This is not obligatory, however, and it is also possible that in principle, a breath indicator displays a respiratory action as an alternative or in addition acoustically, tactilely, or in some other way.

The above-mentioned aspects and features can be realized independently of one another, but also in combination.

Other advantages, features, properties, and aspects of this invention will be apparent from the following descriptions of a preferred embodiment with reference to the accompanying drawings.

BRIEF DESCRIPTION OF THE DRAWINGS

FIG. 5 shows the insert with the protective device according to the proposal in the state of use;

FIG. 6 shows a cross-section of the protective device according to the invention;

FIG. 12 shows a side view of the readiness indicator according to the invention in a second state;

FIG. 13 shows a perspective view of the readiness indicator according to the invention according to FIG. 12 in its position incorporated in the insert-base part;

FIG. 14 shows a side view of the insert-base part according to FIG. 12;

FIG. 15 shows a cross-section of the insert-base part according to FIG. 12;

DETAILED DESCRIPTION OF THE INVENTION

In the figures, the same reference numbers are used for identical or similar parts, wherein corresponding or comparable properties and advantages can be achieved, even if a description is not repeated.

Figure 1:
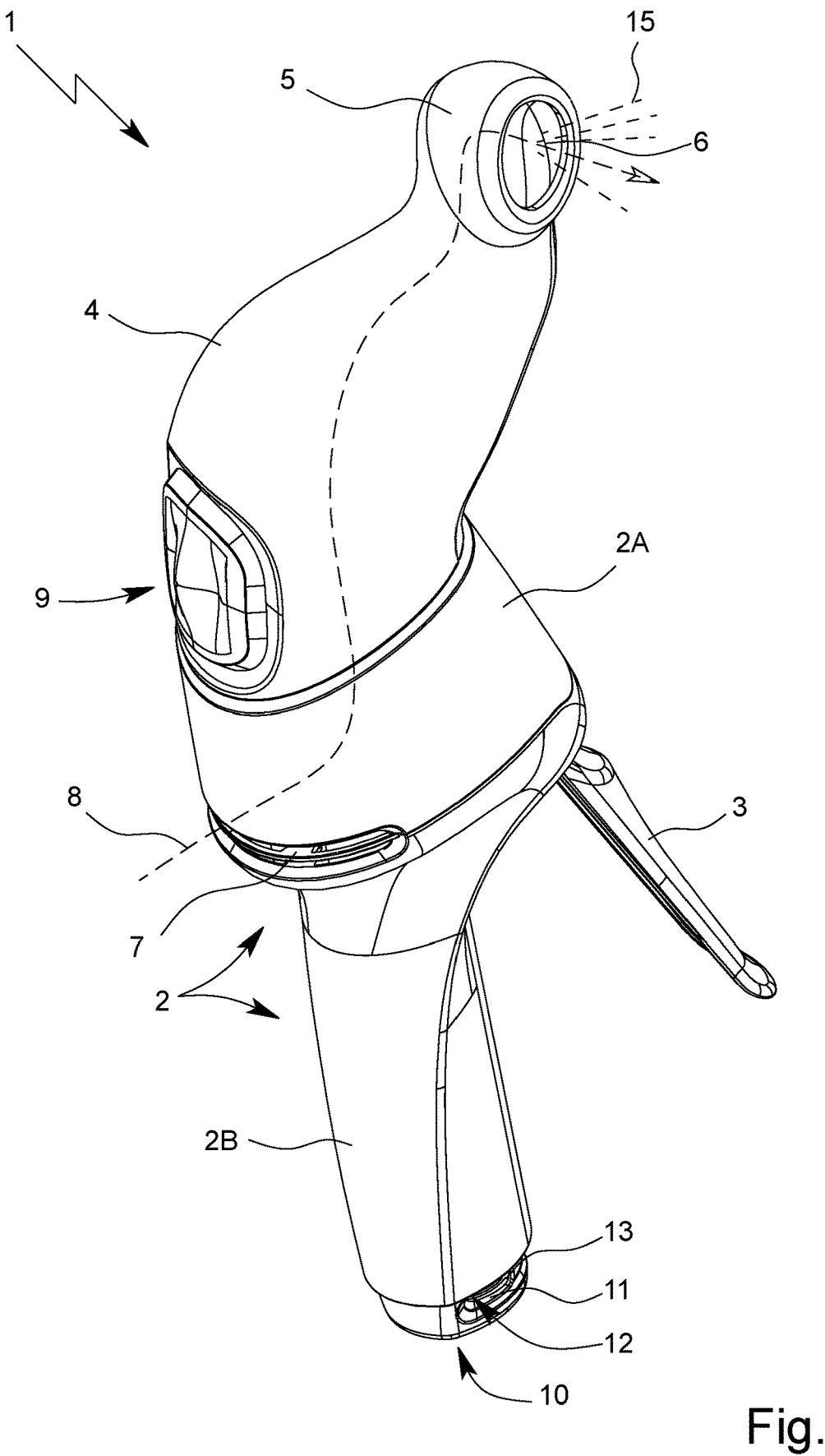
FIG. 1 shows a perspective view of an inhaler according to the invention.

FIG. 1 shows a perspective view of an inhaler 1 according to the invention.

The inhaler 1 according to the invention has a housing 2. In the illustrative example, the housing is divided into a housing-upper part 2A and a housing-grip part 2B. The housing-upper part 2A can be connected to the housing-grip part 2B and/or formed in one piece.

In the illustrative example, the inhaler 1 has an actuating lever 3. The inhaler 1 is preferably designed to trigger the inhaler 1 with the actuating lever 3 and/or to put the inhaler 1 into a ready-to-trigger state. For this purpose, the actuating lever 3 is pivotably mounted on the housing 2. Here, however, other solutions are also possible.

The inhaler 1 preferably has a chamber 4. The chamber 4 is designed to receive, intermediately store, and/or prepare an aerosol 15 formed with a medication.

The inhaler 1 has a dispensing device 5, via which the aerosol 15 can be dispensed. The dispensing device 5 is in particular an adapter for a respiratory opening of a living creature, i.e., a human or an animal, in particular for a nostril or nose.

The inhaler 1 or the adapter device 5 preferably has an outlet 6, via which the aerosol 15 formed with the medication can be dispensed. The outlet 6 is in particular an opening of the chamber 4 and/or dispensing device 5. In the illustrative example, the outlet 6 is formed on an end side on the dispensing device 5 and communicates with the chamber 4, whereby aerosol 15 received in the chamber 4 can be dispensed from the chamber 4 by the dispensing device 5 from the outlet 6.

The inhaler 1 preferably has an air intake 7, via which ambient air can be drawn in. The ambient air flows through the air intake 7 into the chamber 4 and through the dispensing device 5 from the outlet 6, when an underpressure is generated on the outlet 6 because of a respiratory action. In this way, the air flow 8 indicated in dotted lines in FIG. 1 is formed.

In the chamber 4 and/or dispensing device 5, preferably a breath indicator 9 is provided. The design and the function of the breath indicator 9 are dealt with in a more detailed manner at a later time.

The inhaler 1 according to the invention preferably has a display 10. The display 10 makes it possible in particular to depict one or more operating parameters of the inhaler 1. For this purpose, the housing 2, in particular the housing-grip part 2B, has a housing window 11 through which the display 10 can be seen from outside.

In particular, the inhaler has a dose indicator 12. The dose indicator 12 in turn can have a dose indicator window 13, which is arranged preferably aligned with the housing window 11, so that in use the display 10 of the dose indicator 12 can be seen from outside.

Figure 2:
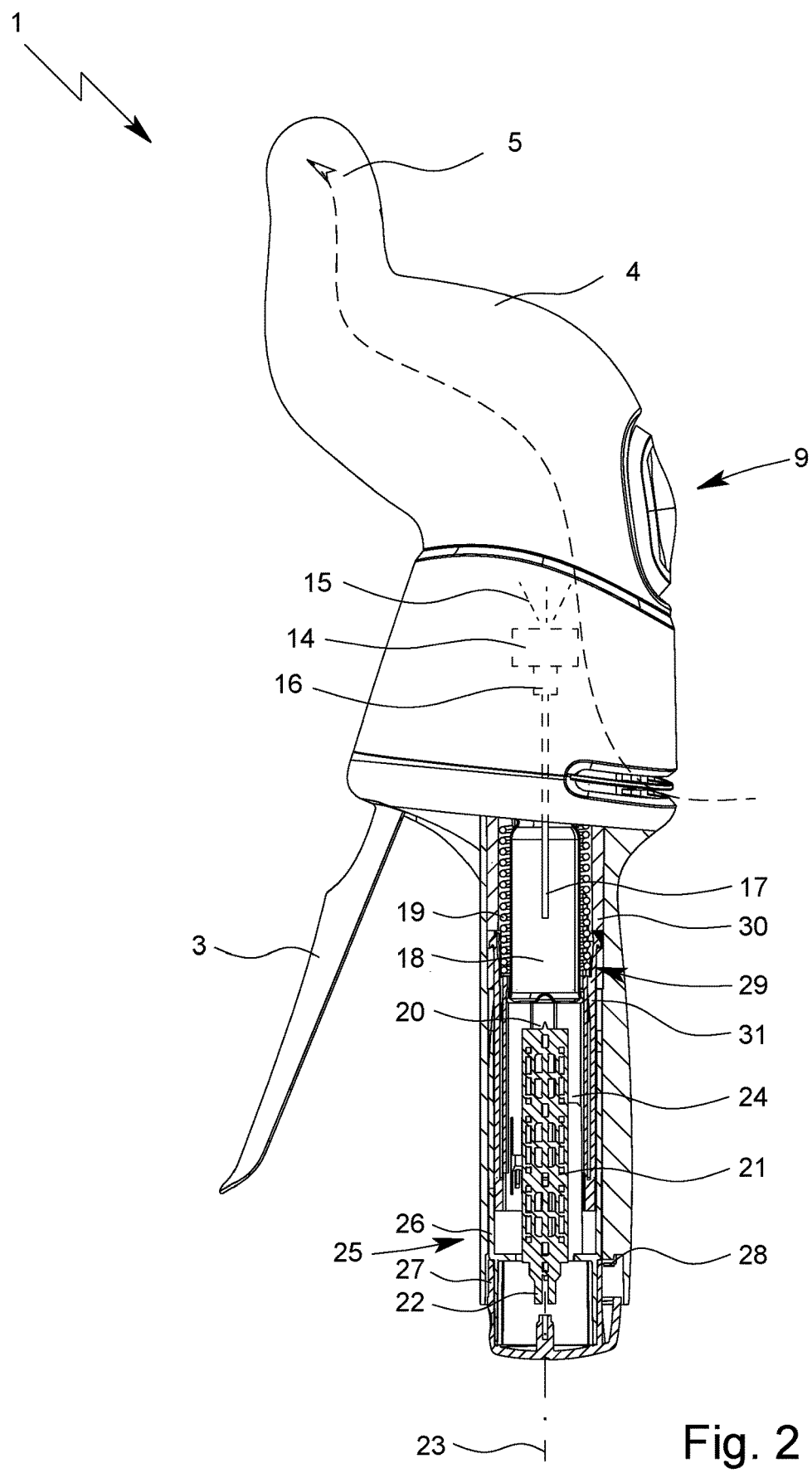
FIG. 2 shows a partial section of an inhaler according to the invention.

FIG. 2 shows the inhaler 1 according to the invention in a partially diagrammatically simplified and partially cut-away view. A discharge nozzle 14 of the inhaler 1, with which aerosol 15 can be formed, is depicted diagrammatically simplified.

The cartridge 18 preferably forms a reservoir for the medication. A typical cartridge 18, as disclosed in International Patent Application Publication WO 96/06011 A1 and corresponding U.S. Pat. No. 5,833,088, contain a volume of approximately 2 to 10 ml. The cartridge 18 is preferably designed rigidly, wherein the medication can be received in a collapsible bag in the cartridge 18.

The cartridge 18 is preferably designed essentially cylindrical and preferably securely integrated into the inhaler 1, in particular so that a removal or a change is impossible or at least is not possible without destruction or damage. It is thus preferred that the inhaler 1 be a single-use or disposable product. Other configurations are also possible, however.

The cartridge 18 preferably has a floor-side, gas-tight seal, which is tapped for aeration upon first use of the inhaler 1. It is to be noted that upon tapping or upon first aeration, only the outside shell of the cartridge 18 is opened. The bag preferably remains undamaged during the necessary aeration. When the medication is removed from the bag, the bag can collapse, and for pressure compensation, ambient air can flow back into the cartridge 18 via an aeration or tapping opening.

An energy storage 19, preferably a tensioning element such as a mainspring, is preferably incorporated pretensioned in order to achieve a high delivery pressure. With the inhaler 1 according to the invention, the pressurization and delivery of the medication during the spraying process is preferably done exclusively by energy stored in the tensioning element, in particular spring force.

The inhaler 1 is thus preferably designed in such a way that the formation of aerosol is independent of a tensioning process, even if prior tensioning can be a requirement for the formation of aerosol. Preferably, the inhaler 1 is designed in such a way that the formation of aerosol, in particular the dose, the discharge rate and/or the discharge speed, is/are independent of the tensioning process and/or are not affected by the tensioning process. In this way, a reliable metering can be achieved.

The inhaler 1 preferably has a conveying device and/or a pressure generator 16 for conveying and nebulization of the medication, in particular in each case in a predetermined, optionally adjustable metered amount, or for metered or meterable nebulization. The inhaler 1 can thus dispense the medication in multiple defined doses, preferably as an aerosol 15. Preferably, in each case one dose can be administered with an actuation of the inhaler 1.

The inhaler 1 and/or pressure generator 16 is designed in particular in such a way that the delivery, pressure generation, and/or spraying is/are done without propellant, mechanically, and/or by the energy or force of an energy storage 19, in particular a spring energy store, especially preferably by the spring force, by a mainspring, spiral spring or another tensioning element. However, other design approaches are also possible. In this case, it is preferred that the nebulization be done independently of a manual operation, in particular independently of the speed of an actuation of the inhaler 1, or driven exclusively by the energy stored in the energy storage 19 and/or tensioning element.

The inhaler 1 and/or pressure generator 16 preferably has a pump device, with a holder for the container and/or with a conveying element, preferably with a conveying pipe 17 being designed as a capillary and having an optional valve, in particular a nonreturn valve. The pump device is thus preferably an assembly of the pressure generator 16, which has the conveying pipe 17 and means for its movement.

The pressure generator 16 can also have the pressure chamber and/or the discharge nozzle 14, in particular in a transition area to the pressure chamber. The pump device can be movable and/or drivable, in particular by the tensioning element. It is preferred that the pump device for discharge of the medication be drivable exclusively by the tensioning element.

The cartridge 18 is fixed in the inhaler 1, preferably via a holder, in particular in a clamping or latching manner, in such a way that the conveying pipe 17 plunges into the container. In this case, the holder can be designed in such a way that the container can be fixed in a non-detachable manner, preferably in a latching manner. The holder can be movable with the container, preferably for loading the energy storage 19 in one direction and induced by the energy storage 19 in an opposite direction, wherein the medication is nebulized.

The inhaler 1 preferably has an actuating lever 3 for loading the energy storage 19 and/or for triggering. The actuating lever 3 is designed for preferably axial tensioning of the tensioning element, in particular via one or more levers which deflect a pivoting movement of the actuating lever 3. Upon tensioning the tensioning element, the pump device is preferably moved downward with the container, and the medication—more precisely, the next dose—is drawn off from the cartridge 18 into the pressure chamber of the pressure generator 16 via the nonreturn valve.

Upon subsequent relaxing of the tensioning element, in particular after actuation of a triggering device, the medication is pressurized in the pressure chamber. To this end, the pump device or the conveying pipe 17 can be moved upward again, wherein the nonreturn valve is now closed, by relaxing of the tensioning element and can now act as a compression die. Preferably, to this end, the pump device is shifted linearly and/or axially with the conveying pipe 17, in particular exclusively, by the tensioning element. This pressure expels the pharmaceutical agent preparation through the discharge nozzle 14, wherein it is formed into the preferably respirable aerosol 15. The triggering device can be formed by the actuating lever or be provided separately as a button or the like.

The breath indicator 9 is preferably designed to display respiratory action by deformation and/or movement. In particular, the breath indicator 9 is designed to display a pressure differential between the interior space and the surrounding area of the chamber 4.

The breath indicator 9 can be designed flat, flexible, deformable, curved, dome-shaped and/or membrane-like. In this way, it is made possible that even comparatively small pressure differentials lead to a deformation and/or movement in order to display the respiratory action. The breath indicator 9 can, preferably in contrast to the chamber 4, be nontransparent, translucent or opaque. This facilitates the reading.

The breath indicator 9 can be designed to be deformed at least partially vault-shaped or dome-shaped or curved in some other way by breathing into, from or through the chamber 4. In this case, a peak or vault can be formed, in particular by a pressure differential between the interior space and the surrounding area of the chamber 4 acting on the breath indicator 9 and the breath indicator 9 being hereby deformed in a corresponding way.

In the case of breathing from or through the chamber 4, the peak can be facing the interior space of the chamber 4. Starting from a rest position of the breath indicator 9, a concave deformation is thus formed. In this case, it has to be taken into consideration that the chamber 4 preferably has rounded walls, and thus a concave deformation of the breath indicator 9 is in particular already present if a convex basic shape is at least partially compensated for. Especially preferred, however, is a deformation upon inhalation from or through the chamber 4 and/or in the case of underpressure in the chamber 4 relative to the surrounding area, in which as a result, the concave deformation also leads to a concave surface in the area of the breath indicator 9.

The breath indicator 9 is preferably designed in such a way that, upon breathing into the chamber 4 and/or in the case of overpressure in the chamber 4 relative to the surrounding area, it is deformed or curved convexly and/or in such a way that the peak is formed on a side facing away from the interior space of the chamber 4. In this case, it can be provided that the convex deformation builds on an already convex basic shape in a rest position or the like of the breath indicator 9, i.e., a convex basic shape is made even more convex by the convex deformation.

Other forms of a deflection of the breath indicator 9 are also possible, however, which are directed in the direction of the interior space of the chamber 4, upon breathing from or through the chamber 4 and/or in the case of underpressure in the chamber 4, and/or which are directed toward the outside and/or in a direction facing away from the interior space of the chamber 4 upon breathing into the chamber 4 and/or in the case of overpressure in the chamber 4 relative to the surrounding area.

It is thus preferred that the breath indicator 9 can be deflected at least partially under the action of breathing into, from, and/or through the chamber 4. The deflection preferably takes place by material deformation or material expansion. This preferably takes place elastically and/or reversibly, so that an indication of a respiratory action can be performed several times. A material deformation and/or material expansion or other movement or deflection of the breath indicator 9 is preferably more than 1 mm, in particular more than 2 mm or 3 mm.

The inhaler 1 preferably has the inhalation valve, which automatically closes under the action of breathing into the chamber 4. The dispensing device 5 is preferably designed for insertion into a body orifice, in particular into a nose hole or nostril. Therefore, an exhalation process can be carried out through an alternative body orifice, such as another nose hole or the like.

In an exhalation process, preferably an overpressure or dynamic pressure results in the chamber 4. The pressure differential prevailing at the breath indicator 9 due to the dynamic pressure in the chamber 4 can be less than 50 hPa, preferably less than 40 hPa or 30 hPa, in particular between 5 hPa and 15 hPa, relative to the surrounding area of the chamber 4. Therefore, it is preferred that the breath indicator 9 be designed to make possible a curvature, deformation, and/or deflection outward in the case of corresponding pressure differentials, which allow a non-destructive indication of a respiratory action, in particular curvature, deflection, and/or deformation of more than 0.5 mm and/or less than 10 mm.

The breath indicator 9 can be inserted or insertable, preferably by positive engagement, into the chamber wall. Further, the breath indicator 9 can be connected tightly, in particular airtight or pressure-tight, to the chamber wall, and injection-molded, glued, welded or clamped on the chamber wall. As an alternative, the breath indicator 9 can also be formed by the chamber wall. A tight fastening of the breath indicator 9 to the chamber wall has the advantage that the breath indicator 9 according to the invention draws no secondary air, which would be disadvantageous for the transport of aerosol and furthermore could lead to active ingredient losses via eddying of the aerosol 15 guided in the chamber 4.

The breath indicator 9 is preferably arranged outside of the flow; i.e., it does preferably not impede the air flow 8 through the chamber 4 and/or the dispensing of aerosol. The inhaler 1 is preferably closed and/or designed airtight between the intake opening of the chamber 4 and an outlet 6 of the dispensing device.

The breath indicator 9 and the chamber wall can have different materials and/or material thicknesses. In this case, it is preferred that the material of the breath indicator 9 be more flexible, expandable more easily, and/or thinner than the material of the chamber wall. This makes possible a movement and/or deformation of the breath indicator 9, whereby respiratory action can be displayed.

The breath indicator 9 can have a connecting means for fastening in a breakthrough of the chamber wall. The breath indicator 9 can thus be inserted or insertable into a breakthrough of the chamber wall. Preferably, the breath indicator 9 has a membrane frame 53 which can bound the breath indicator 9 and can have a contour that corresponds to a boundary and/or an opening frame 55 of the breakthrough of the chamber wall.

The membrane frame 53 or another connecting means is preferably designed for airtight and/or pressure-tight connection of the breath indicator 9 to the chamber wall. The connecting means can encompass a boundary of the breakthrough of the chamber wall, or the boundary of the breakthrough of the chamber wall is designed for encompassing the edge or membrane frame 53 of the breath indicator 9. As an alternative or in addition, the membrane frame 53 can be glued to the chamber wall.

The breath indicator 9 can have a surface area that is larger than 0.5 $cm^2$, preferably larger than 1 $cm^2$, in particular larger than 2 $cm^2$, and/or smaller than 25 $cm^2$, preferably smaller than 20 $cm^2$, in particular smaller than 15 $cm^2$.

The breath indicator 9 can, without a pressure differential between the inner and outer sides, continue a surface line or contour line of the chamber wall adjoining the breath indicator 9 and/or align with the chamber wall adjoining the breath indicator 9. This makes possible an outside shape of the chamber 4 that is uniform in a rest state without a pressure differential; this reduces susceptibility to contamination and furthermore is also aesthetically advantageous.

The breath indicator 9 can have a sealing surface for abutting on a boundary of the breakthrough, wherein the sealing surface is designed to abut tightly on the boundary of the breakthrough when the wall section is inserted into the breakthrough.

The breath indicator 9 can have an elastomer, latex, nitrile rubber, neoprene, polyurethane, styrene-ethylene-butadiene-styrene, styrene-butadiene rubber and/or silicone, or can at least be essentially formed therefrom.

The breath indicator 9 can be arranged at a distance of more than 2 cm, preferably more than 3 cm, and/or less than 20 cm, preferably less than 15 cm, from the outlet 6 and/or the intake opening.

The breath indicator 9 is preferably designed for a continuous display of the respiratory action and/or pressure change between the interior space of the chamber 4 and the surrounding area. In particular, breathing into, from, and/or through the chamber 4 leads to a continuous pressure fluctuation corresponding to the respiratory action. Such a continuous pressure fluctuation can advantageously be displayed continuously by the breath indicator 9 according to the invention.

When the medication is nebulized, the preferably respirable aerosol 15 is formed, which can be breathed in or inhaled by a not-depicted user or patient, such as an animal, human, or preferably a large animal, in particular a horse. Usually, the inhalation is done at least once daily, in particular several times daily, preferably at predetermined time intervals, in particular depending on the disease.

The aerosol 15 can be intermediately stored in the chamber 4 of the inhaler 1 and/or can be dispensed by the dispensing device 5. In this case, the dispensing device 5 is designed for fluidic connection of the chamber 4 with a body orifice, preferably a nostril, in particular of a horse. The dispensing device 5 has the outlet 6, via which the aerosol 3 can be dispensed. In the illustrative example, the dispensing device 5 is formed in one piece with the chamber 4 or connected to the latter. This is not obligatory, however.

The chamber 4 is preferably designed for receiving and/or intermediately storing the aerosol 15 that is generated by the inhaler 1. The chamber 4 is arranged or can be arranged preferably at least essentially downstream from the discharge nozzle 14.

The chamber 4 and the dispensing device 5 can be formed separately and/or in multiple pieces. In the illustrative example, the chamber 4 is formed as an integral piece with the dispensing device 5, in particular an adapter for a body orifice, in particular a nose or nostril. In this way, recesses and gaps, to which contaminants can adhere or in which they can enter, can be avoided.

In the illustrative example, the introduction of aerosol 15 into the chamber 4 is done in the spraying direction of the discharge nozzle 14.

The chamber 4 is designed preferably at least essentially dimensionally stable. However, the chamber 4 in principle can be designed to be at least essentially rigid, elastic, and/or flexible. In the illustrative example, the chamber 4 is formed from a dimensionally-stable, flexible, reversibly deformable material and turns into the dispensing device 5 without any transition in terms of fluidics in order to ensure a continuous path of flow.

The dispensing device 5 is preferably designed as a nose adapter for insertion into the nostril of a horse or some other animal, in particular a large animal.

The chamber 4 and/or the dispensing device 5 can be transparent or partially transparent, in particular formed from transparent or partially transparent plastic. In this way, the formation of aerosol can be controlled. The plastic is in particular clear or colored and translucent.

The dispensing device 5 preferably has an outlet 6 here, which engages or can be inserted into the nostril and/or a nasal passage of the horse or another body orifice, and can connect the chamber 4 and/or the dispensing device 5 can fluidically connect to the body orifice. Especially preferably, the dispensing device 5 is designed in such a way that the outlet 6 always ends in the correct nasal passage and not in a dead end. The dispensing device 5 can be designed at least essentially as described in International Patent Application Publication WO 94/17753 A1 and corresponding U.S. Pat. No. 5,666,948 A.

The user or patient, in particular a horse, can inhale the aerosol 15, wherein preferably air can be drawn through the chamber 4.

The chamber 4 preferably has a volume of more than 0.05 l, in particular more than 0.1 l, especially preferably approximately 0.1 to 0.4 l. Preferably, the size of the chamber 4 is matched to the inhaler 1 in such a way that the aerosol 15 that is generated upon actuation of the inhaler 1 can be received at least essentially completely by the chamber 4, in particular without the aerosol 15 or the sprayed pharmaceutical agent preparation significantly precipitating or depositing on the inside wall of the chamber.

For the purpose of forming the aerosol 15, the inhaler 1 can have a pressure generator 16. The pressure generator 16 is preferably designed to convey medication to the discharge nozzle 14 so that the latter forms the aerosol 15 herewith.

In the illustrative example, the pressure generator 16 is realized as a pump. The pressure generator 16 can be connected and/or formed in particular with a conveying pipe 17. In the illustrative example, the pressure generator 16 is formed with use of the conveying pipe 17, by the conveying pipe 17 having a nonreturn valve and acting as a piston in the pressure generator 16. In principle, however, the pressure generator 16 can also be realized differently.

The inhaler 1 according to the invention has a cartridge 18. The cartridge 18 contains a medication or is designed therefor. The medication is in particular a liquid. This liquid contains a pharmacologically effective active ingredient. The present invention, however, can also be applied to other inhalers and in particular also to powder inhalers.

The inhaler 1 preferably has an energy storage 19. In the illustrative example, the energy storage is designed as a spring, in particular a coil spring. In principle, however, the energy storage 19 can also be implemented differently, for example as a compressed air reservoir or the like. It is preferred, however, that the energy storage 19 can intermediately store energy that is or can be expended by a user in order to provide the latter subsequently for the generation of pressure for the purpose of dispensing the aerosol 15. In general, the pressure generator 16 is thus preferably supplied with energy by the energy storage 9, so that the pressure generator 16 conveys the medication to the discharge nozzle 14 and the discharge nozzle 14 as a result forms the aerosol 15 with the medication.

The cartridge 18 can be sealed in the delivery state and can be tapped by means of a tapping element 20 of the inhaler 1 for preparing an operating readiness in order to make possible an aeration and/or to be connected with the conveying pipe 17 for the purpose of removing the medication.

The cartridge 18 preferably contains an inside bag (not depicted), which can be aerated by tapping the cartridge on the side that faces away from the medication, which facilitates a collapsing of the inside bag. In this way, the build-up of an excessive underpressure in the cartridge is avoided, which is conducive to a reliable and precise delivery of the medication.

The inhaler 1 according to the invention preferably has a pin 21. The pin 21 has the tapping element 20 on the side facing the cartridge 18. Here, however, other solutions are also possible.

As an alternative or in addition, the pin 21 has an actuation section 22 which is designed to actuate the dose indicator 12. By actuating the dose indicator 12, the latter is driven, so that the dose indicator 12 counts doses of the medication that were already administered or can still be administered, and displays the latter or a value corresponding thereto.

The pin 21 is preferably movable along a longitudinal axis 23 upon actuation of the inhaler 1, preferably linearly and/or in translatory manner. In this case, with the tapping element 20, it comes into contact with the cartridge 18, in such a way that the cartridge 18 is tapped. As an alternative or in addition, the pin 21 acts by means of the actuation section 22 in such a way on the dose indicator 12 that the latter is actuated.

The pin 21 can be moved by a movement of the cartridge 18 in order to direct the movement of the cartridge 18 to the dose indicator 12. The pin 21 is, in this respect, a spacer for bridging a distance between the cartridge 18 and the dose indicator 12 and/or an adapter for adapting the dose indicator 12 to the cartridge 18 in such a way that a movement of the cartridge 18 can actuate the dose indicator 12.

The inhaler 1, in particular the housing-base part 2B, preferably has a supporting device 24 for the pin 21. The supporting device 24 corresponds in such a way to the pin 21 that the latter is supported linearly along the longitudinal axis 23. Therefore, the pin 21 can accordingly move in a translatory manner inside the inhaler 1, for example in order to tap the cartridge 18 with the tapping element 20 and/or to actuate the dose indicator 12. This will be explained in greater detail below.

The inhaler 1 preferably has an insert 25. The insert 25 preferably forms a part of the housing 2, in particular the housing-grip part 2B.

The insert 25 can have an insert-upper part 26 and an insert-base part 27. The insert 25 can thus be made in multiple parts. In this case, the insert 25 preferably has the dose indicator 13, the pin 21, and/or the supporting device 24.

In the illustrative example, the dose indicator 13 is arranged in the insert-base part 27, while the supporting device 24 is formed by the insert-upper part 26. In this way, a simple assembly can be created. The parts of the insert 25 are preferably permanently connected to one another, in particular positively and/or by bonding.

The insert 25 optionally has a tamper-proof seal 28. In the illustrative example, the tamper-proof seal 28 is formed by a predetermined breaking point, which breaks upon movement of the insert 25 into the housing. To this end, the tamper-proof seal 28 can tap on a section of the housing 2 and break as soon as the insert 25 is pushed into the housing 2, in particular in the housing-grip part 2B.

The inhaler 1, especially the housing 2 of the inhaler 1, preferably has a slide-in guide 29. The slide-in guide 29 is designed to guide the insert 25, so that the latter can be inserted into the housing 2. The slide-in guide 29 is then formed in a manner that is preferably corresponding and/or complementary to the insert 25.

In particular, the insert 25 and the slide-in guide 29 are formed in a corresponding manner to one another such that the insert 25 can be pushed (only) in a translatory or linear manner into the and/or over the slide-in guide 29. The slide-in guide 29 preferably corresponds to the insert 25 in such a way that a rotation of the insert 25 is blocked. This can be achieved in that the insert 25 and/or the slide-in guide 29 are not completely round in cross-section on surfaces that glide along one another.

The slide-in guide 29 is preferably formed with a housing part 30 or connected to the housing part 30, which is part of the housing 2 or is firmly connected thereto.

The inhaler 1 preferably has a protective device 31. The protective device is preferably designed to be damaged and/or to provoke damage when the inhaler 1, in particular its housing 2, is tampered with. In turn, this damage is preferably such that because of the damage, further use of the inhaler 1 for dispensing the medication is prevented. The inhaler 1 is consequently rendered unusable by the damage to the protective device 31.

The inhaler 1 is unusable even when the protective device 31 can be repaired or replaced, and the inhaler 1 subsequently may function again, i.e., the medication can thus be dispensed (properly) with it again. In terms of the present invention, repairing or replacing the protective device 31 is a remanufacturing of the inhaler 1, so that the inhaler 1 is unusable because of the damage unless it is remanufactured. The inhaler 1 is thus unusable when it can be put into operation again only by repairing or replacing the protective device 31.

The protective device 31 is explained in more detail below using FIGS. 3 to 6.

Figure 3:
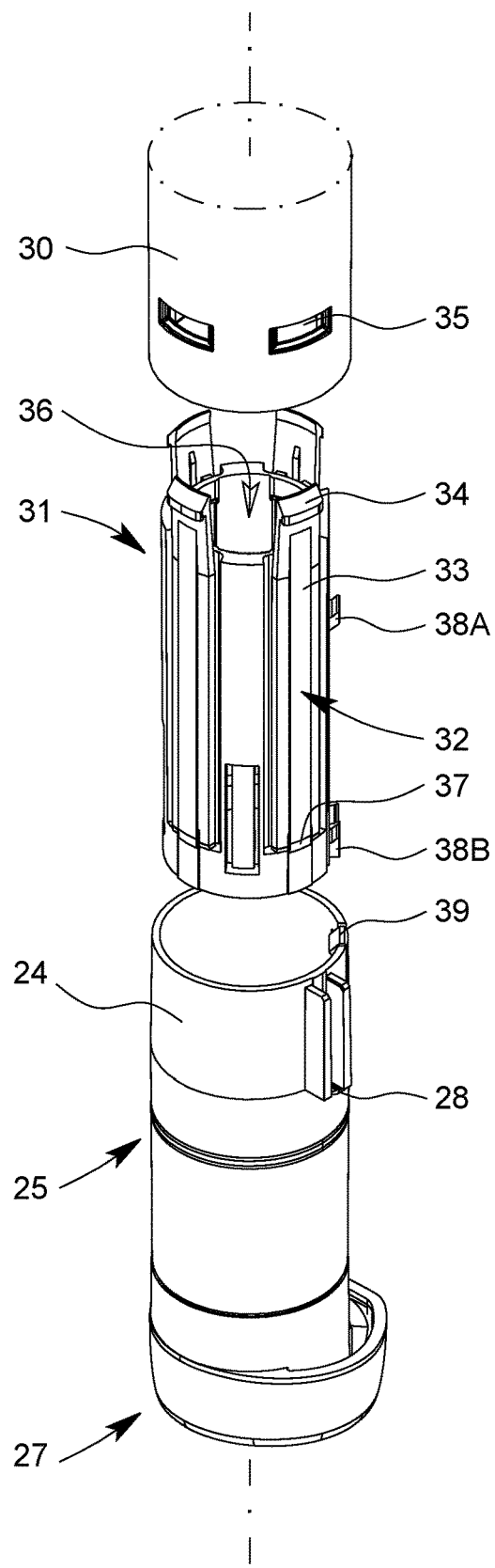
FIG. 3 shows an exploded view of the insert with the protective device according to the invention.

In an exploded view, FIG. 3 shows the protective device 31 according to the invention as well as the insert 25 and the housing part 30 in sections. In the illustrative example, the protective device 31 can be connected to the housing part 30 and in this way forms the slide-in guide 29. Here, however, in principle, other solutions are also possible, even when this solution has proven to be especially advantageous.

As already previously explained in principle, the protective device 31 has one or more structural measures to provoke damage when tampering with the inhaler 1 for the purpose of removing or replacing the cartridge 18, which damage leads to the unusability of the inhaler 1.

For this purpose, the protective device 31 preferably has one or more fastening devices 32 which are designed to provoke damage when the inhaler is tampered with for the purpose of removal or replacement of the cartridge 18. In particular, the fastening device(s) 32 is or are designed and arranged in such a way that a separating action on the housing-grip part 2B, in which the cartridge 18 is received, leads to the described damage.

The fastening device(s) 32 preferably has or in each case have an arm 33. This respective arm 33 extends along or parallel to the longitudinal axis 23 and accordingly along the housing-grip part 2B. When now a separating action on the housing-grip part 2B is exerted, for example a sawing, the arm 33 provokes severing of itself because of its extension. With one or more severed arms 33, the inhaler 1 is rendered unusable.

Thus, the inhaler 1 with the protective device 31 can be designed to ensure that, when an arm 33 is severed, the slide-in guide 29 is no longer capable of guiding the insert 25 properly and as a result, further use of the inhaler 1 is prevented. In this connection, it has turned out to be advantageous that the slide-in guide 29 is formed by or with the protective device 31, and the damage can thus make the slide-in guide 29 unusable.

The arm 33 or the arms 33 has or have in each case preferably a latching element 34. The latching element 34 is especially preferably arranged at the open end of the arm 33. This is not required, however.

The protective device 31 is preferably fastened to the housing part 30 with the latching element(s) 34. In the illustrative example, the protective device 31 forms the slide-in guide 29 by fastening on the housing part 30. The protective device 31 is preferably designed to lose the fastening on the housing part 30 by separating one arm 33. In particular, by separating the arm 33, the latching element 34 is separated from the rest of the protective device 31, so that the latter is not—or is no longer—held completely on the housing part 30.

When the protective device 31 is no longer held—or no longer held completely—on the housing part 30, this impairs the function of the slide-in guide 29 or a part of the latter in the illustrative example in such a way that further use of the inhaler 1 for dispensing the medication is prevented.

The fastening device(s) 32 can have or represent predetermined breaking points. In this way, the damage to the protective device 31 can be evoked when there is an attempt to tamper with the insert 25 for the purpose of removing or replacing the cartridge 18. In particular, the protective device 31 is set up in such a way that one or more fastening devices 32, arms 33 and/or latching elements 34 tear off when the insert 25 if forcibly pulled on. In this way, further use of the inhaler 1 for dispensing the medication is prevented.

The housing part 30 preferably has one or more complementary latching elements 35. In the functional state of the inhaler 1, the latter form a connection with the latching element 34 or the latching elements 34 of the protective device 31, whereby the protective device 31 is fastened to the housing part 30. The damage to the arm 33, the latching element 34 and/or the fastening devices 32 then leads to the protective device 3 no longer being properly fastened to the housing part 30 and the function of the inhaler 1 being impaired.

The protective device 31 preferably has a receiving device 36. The receiving device 36 is preferably designed for receiving and/or guiding the cartridge 18. In particular, the receiving device 36 is tubular or sleeve-like. The receiving device 36 preferably has a form that makes it possible to shift the cartridge 18 in the state received in the receiving device 36. The receiving device 36 and the cartridge 18 are therefore preferably formed in a manner corresponding and/or complementary to one another, in particular so that the cartridge 18 can be inserted with play in the receiving device 36.

The protective device 31 preferably has a fastening region 37, in which the arm 33 or the arms 33 are connected to the receiving device 36. In particular, the arm 33 or the arms 33 in the fastening region 37 are formed as an integral piece with the receiving device 36.

Altogether, the protective device 31 in the exemplary embodiment is thus a tubular or sleeve-like receiving device 36, on which one or more arms 33 are arranged in the fastening region 37, which arms each carry a latching element 34 on an end facing away from the fastening region 37. By damaging or separating one or more arms 33 and/or latching elements 34, the protective device 31 is automatically separated completely or partially from the housing part 30, and in this way, the inhaler 1 is rendered unusable for the further dispensing of the medication.

The protective device 31 preferably has one or more holding elements 38, in particular a first latching element 38A and a second latching element 38B. The holding element(s) 38 is/are designed and set up to secure the insert 25 against being removed from the housing 2.

In particular, multiple holding elements 38 are provided at various positions, in particular in the positions lying behind one another in the direction of the longitudinal axis 23, so that the insert 25 is first held with one of the holding elements 38 in a first latching position, in which the insert 25 is not yet inserted, and so that the insert 25 attains from the first latching position to the second latching position upon insertion, in which second latching position the insert 25 is held by a second of the holding elements 38 in the inserted position. For this purpose, the insert 25 preferably has a corresponding and/or complementary holding element 39.

Figure 4:
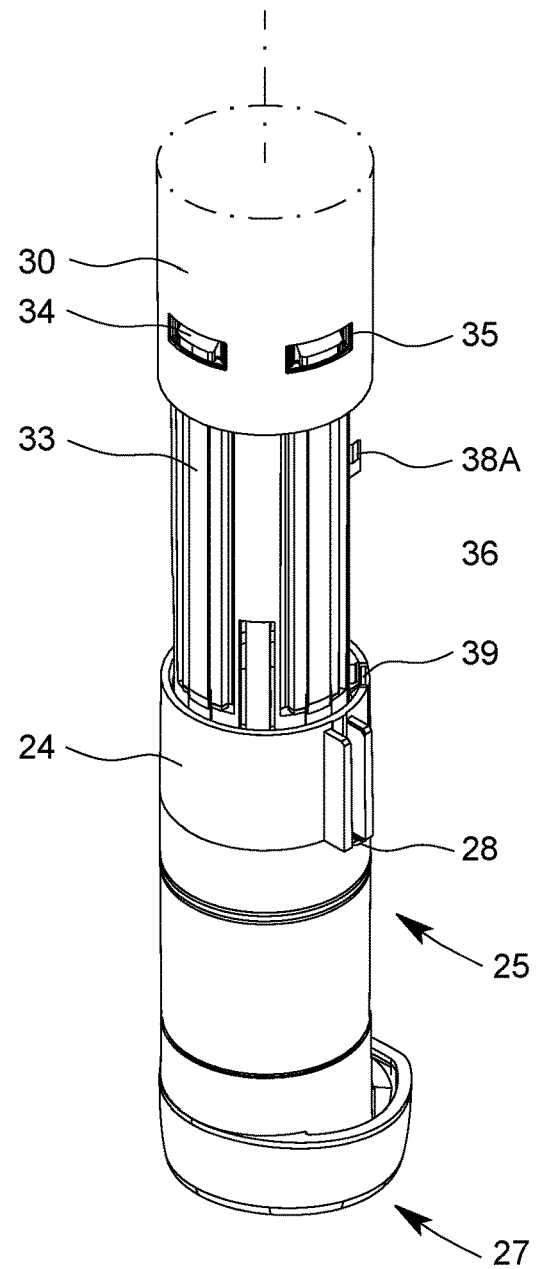
FIG. 4 shows the insert with the protective device according to the invention in the delivery state.

FIG. 4 shows the housing part 30, the insert 25, and the protective device 31 in the delivery state of the inhaler 1. In the delivery state of the inhaler 1 with the insert 25 that is not yet inserted, the holding element 39 is first engaged, with its holding element 39 with the first holding element 38B of the protective device 31 and/or the slide-in guide 29, by which the insert 25 cannot be removed from the housing 2 starting from the non-inserted position.

FIG. 5 shows the same parts as FIG. 4 after the insert 25 has been pushed into the housing 2, in particular the housing-grip part 2B. By this, the inhaler 1 is preferably put into a ready-to-use state, which will be explained in greater detail later. By inserting the insert 25, the insert 25 with its holding element 39 engages with another, second holding element 38A of the protective device 31 and/or the slide-in guide 29, by which the insert 25 is locked in its inserted position.

FIG. 6 depicts a cross-section of the protective device 31 according to the invention. Supplementary to the already explained parts, the protective device 31 and/or its receiving device 36 preferably has one or more stops 40. The stop or stops 40 is/are designed to limit the movement of the cartridge 18 in the receiving device 36.

Via the stop(s) 40, upon clamping the cartridge 18 against this or these stop(s) 40 in the course of preparing the performing of the triggering, a force on the protective device 31 can be produced, which force exerts tensile force on one or more fastening devices 32 of the protective device 31, whereby the force, in particular via the arm(s) 33 and the latching element(s) 34, is dissipated into the housing part 30, provided that the protective device 31 is undamaged.

When the protective device, in particular the fastening device(s) 32, is damaged, the force that is exerted by the cartridge 18 via the stop(s) 40 can no longer be dissipated into the housing part 30, whereby the protective device 31 cants with the insert 25 and/or the protective device 31 including the insert 25 is pushed out from the housing 2 by means of the cartridge 18 or without the latter. In this way, further use of the inhaler 1 for dispensing the medication can be prevented.

As indicated in FIG. 6 with the arrow 41, it is preferred that one or more fastening device(s) 32, in particular the arm(s) 33, have pretensioning. In this way, it can be ensured that the latching element(s) 34 is/are engaged securely in the complementary latching element(s) 35. In the illustrative example, the pretensioning is directed radially outward, since the latching element(s) 34 preferably engage(s) in the complementary latching elements 35 from the inside.

Figure 7:
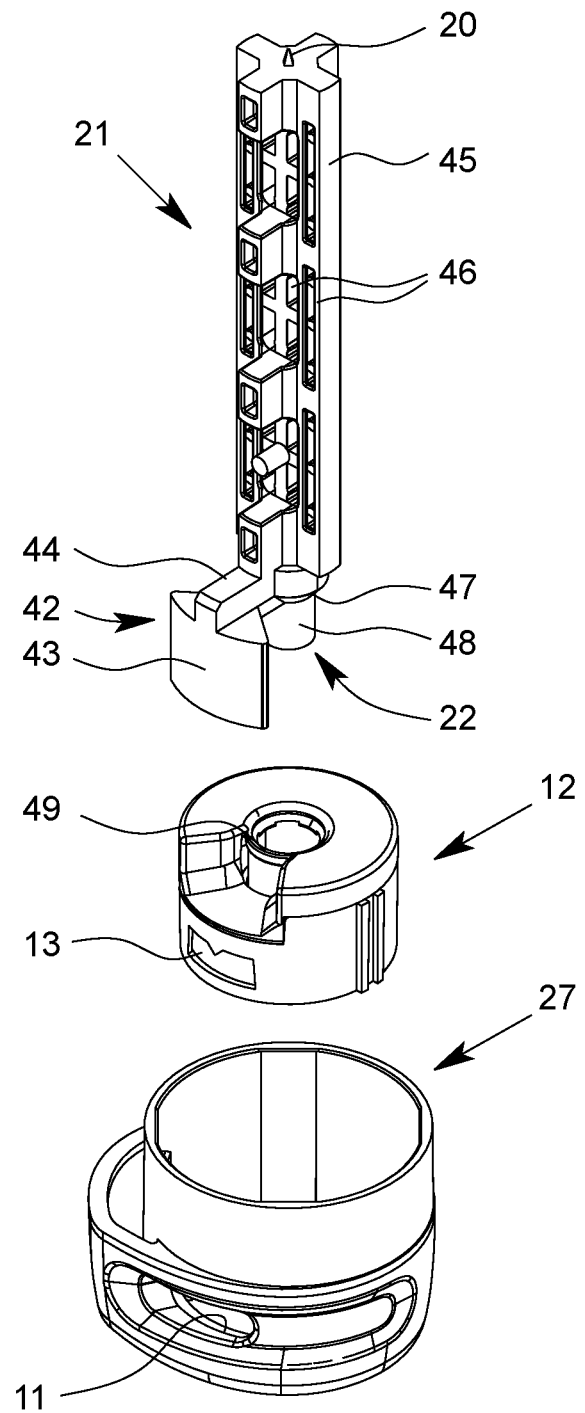
FIG. 7 shows an exploded view of the readiness indicator according to the invention.
Figure 8:
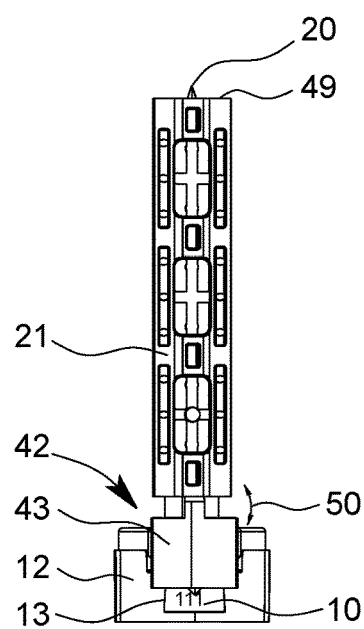
FIG. 8 shows a side view of the readiness indicator according to the invention in a first state.

In an exploded view, FIG. 7 depicts the pin 21 together with the dose indicator 12 and the insert-base part 27.

The inhaler 1 according to the invention preferably has a readiness indicator 42. The readiness indicator 42, according to the invention is designed to display whether the inhaler 1 is, in particular immediately, ready for triggering or not. The inhaler 1 is ready for triggering when it can be triggered by a single action that can be performed in a simple and fast manner, in particular an actuation of a trigger, by which the medication is dispensed and/or the aerosol 15 is formed.

The inhaler 1 is not ready for triggering when it is already triggered and/or else when it still previously has to be prepared to be ready to trigger.

With reference to the specific embodiment, the trigger readiness depends on the energy state of the energy storage 19, in particular on the tensioning state of the spring forming the energy storage 19. When the energy storage 19 is loaded so that it can drive the pressure generator 16 for dispensing the medication, the inhaler 1 is, for example, ready to trigger, whereas the inhaler 1 with an unloaded energy storage 19 and/or untensioned spring is not ready to trigger, because, in this case, the energy storage 19 must first be loaded and/or the spring must first be tensioned, so that the inhaler 1 can be subsequently triggered.

It is understood that depending on the design of the respective inhaler 1, as an alternative or in addition, the trigger readiness can depend on other constraints.

The readiness indicator 42 is preferably designed for optically displaying of the trigger readiness. As an alternative or in addition, however, it can also be displayed in an acoustic or tactile way or in some other way or else in variously combined ways, whether the inhaler 1 is ready to trigger or not.

It is preferred that the readiness indicator 42 display the trigger readiness with the display 10 of the inhaler 1. The readiness indicator 42 can output the trigger readiness through the housing window 11. In particular, the readiness indicator 42 changes the display 10 in the housing window 11 in dependence of the trigger readiness of the inhaler 1.

Further, it is preferred that the readiness indicator 42 share the display with another indicator of the inhaler 1. It is provided in particular that the readiness indicator 42 shares the display 10 with the dose indicator 12. In this way, only one display 10 is to be provided, which is used multiple times.

Especially preferably, the readiness indicator 42 completely or partially conceals the display 10 of the dose indicator 12 in dependence of the trigger readiness of the inhaler 1. For this purpose, the readiness indicator 42 can have a covering element 43 which conceals the display 10 of the dose indicator 12 or another indicator of the inhaler 1 more or less in dependence of the trigger readiness.

It can be provided that in the ready-to-trigger state, the display 10 is completely concealed by the covering element 43, so that the former is no longer visible from outside. In this case, it is preferred that in the not-ready-to-trigger state, the display 10 is less concealed by the covering element 43 or is completely freely visible.

As an alternative, it is possible that in the not-ready-to-trigger state, the display 10 is completely concealed by the covering element 43, so that the former is no longer visible from outside. In this alternative, it is preferred that in the ready-to-trigger state, the display 10 is less concealed by the covering element 43 or is completely freely visible.

Especially preferably, the readiness indicator 42 is implemented by or with the pin 21. With reference to FIG. 7, the pin 21 preferably has the covering element 43. The covering element 43 can be pushed before the dose indicator 12 and/or the dose indicator window 13 by a movement of the pin 21.

In the ready-to-trigger state of the inhaler 1, the cartridge 18 is preferably shifted compared with the not-ready-to-trigger state of the inhaler 1. As already previously explained, the pin 21 can be shifted by the movement of the cartridge 18. In this way, the readiness indicator 42 can be driven indirectly by the movement of the cartridge 18.

With the cartridge 18 being moved, in the specific type of the inhaler 1 according to the invention, the energy storage 19 is loaded and/or the spring that implements the latter is tensioned, by the cartridge 18 and/or an element that holds the cartridge 18 being moved. Thus, one position of the cartridge 18 is characteristic for the ready-to-trigger state of the inhaler 1, and another position of the cartridge 18, which is shifted relative to the one position, is characteristic for the not-ready-to-trigger state.

Accordingly, the pin 21 is designed and arranged in the inhaler 1 in such a way that the movement of the cartridge 18 which accompanies the loading of the energy storage 19 and/or the tensioning of the spring results in the display of the ready-to-trigger state or not-ready-to-trigger state of the inhaler 1.

In particular, it is provided that the pin 21 simultaneously actuates the dose indicator 12 when the readiness indicator 42 changes its state from the display of the not-ready-to-trigger state to the display of the ready-to-trigger state or vice versa.

To this end, it can be provided that the pin 21 has a protrusion 44, by means of which the covering element 43 is arranged offset to the actuation section 22 of the pin 21. In this way, the actuation section 22 can actuate the dose indicator 12, while the covering element 43 conceals or unblocks the display of the dose indicator 12.

For displaying the ready-to-trigger state or not-ready-to-trigger state, it is further preferred that the covering element 43 conceals or uncovers the dose indicator window 13. To this, for display of the ready-to-trigger state or not-ready-to-trigger state of the inhaler 1, the covering element 43 can be inserted between the dose indicator window 13 and the housing window 11, by which the display 10 of the dose indicator 12 is concealed or uncovered. As an alternative or in addition, for displaying the ready-to-trigger state or not-ready-to-trigger state of the inhaler 1, the covering element 43 can be completely or partially removed between the dose indicator window 13 and the housing window 11.

The readiness indicator 42 can thus display the trigger readiness of the inhaler 1 by the degree of concealment of the display 10 by means of arrangement and/or shifting of the covering element 43 between the housing window 11 and the dose indicator window 13.

FIGS. 8 to 11 depict one of the states, in the exemplary embodiment the not-ready-to-trigger state. In the not-ready-to-trigger state, the display 10 is not—or not completely—concealed by the covering element 43 of the readiness indicator 42. Observed from the outside through the housing window 11, the display 10 of the dose indicator 12 can thus be recognized, symbolized with exemplary numbers in FIGS. 8 and 10. In the cross-section of the parts pin 21, insert-base part 27 and dose indicator 12 of FIG. 11, it can be seen that the covering element 43 is arranged at a position in which it does not block the clear view of the display 10 through the housing window 11 and the dose indicator window 13.

FIGS. 12 to 15 depict another of the states, in the exemplary embodiment the ready-to-trigger state. In the ready-to-trigger state, the display 10, unlike in the not-ready-to-trigger state, is partially or completely concealed by the covering element 43 of the readiness indicator 42. Observed from the outside through the housing window 11, the display 10 of the dose indicator 12 thus cannot be recognized, since it is concealed by the covering element 43. Instead, the covering element 43 can be recognized in the dose indicator window 13 and symbolizes the ready-to-trigger state of the inhaler 1. In the cross-section of the parts pin 21, insert-base part 27 and dose indicator 12 of FIG. 15, it can be seen that the covering element 43 is arranged at a position in which it blocks the clear view of the display 10 through the housing window 11 by being arranged in front of the dose indicator window 13.

It is understood that the examples according to FIGS. 8 to 15 can be applied in a corresponding way when the covering element 43 blocks the display 10 in the ready-to-trigger state and uncovers it in the not-ready-to-trigger state.

The covering element 43 is preferably colored, in particular red, for better visualization.

Figure 9:
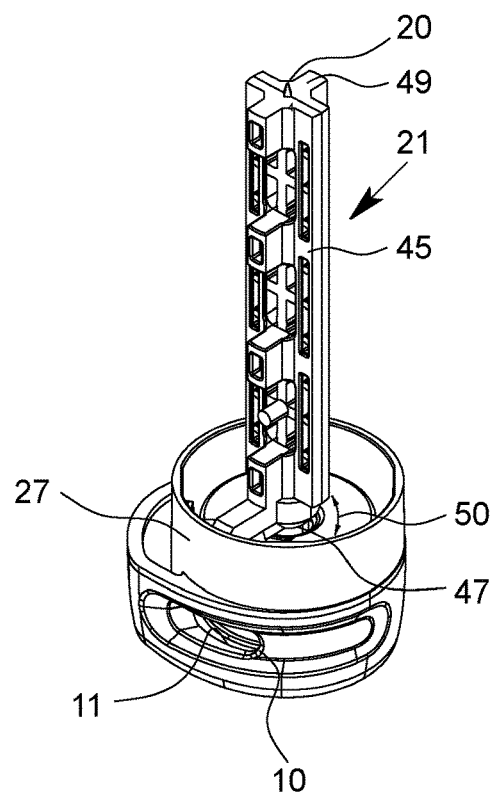
FIG. 9 shows a perspective view of the readiness indicator according to the invention according to FIG. 8 in its position incorporated in the insert-base part.
Figure 10:
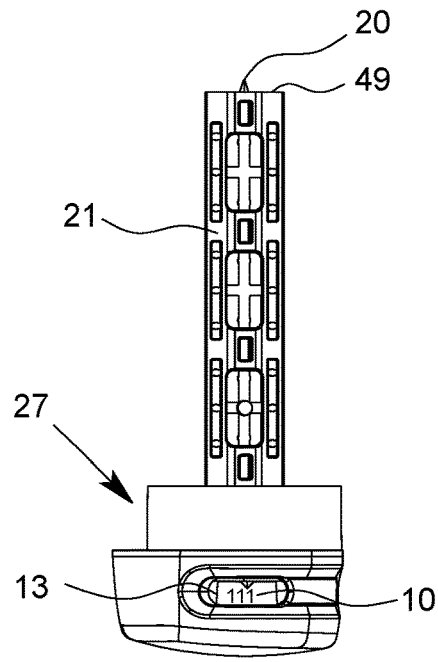
FIG. 10 shows a side view of the insert-base part according to FIG. 9.

With reference to FIGS. 9 and 13, the pin 21 has a guiding device 45, with which the pin 21 is guided in a linear manner and/or secured against rotation. In the illustrative example, the pin 21 is cross-shaped in cross-section. The housing 2 of the inhaler 1 and/or the insert 25, in particular the insert-base part 27, preferably has the positioning device 24, which is complementary or corresponds to the insert-base part 27, for the purpose of guiding the pin 21 in the described way.

Figure 11:
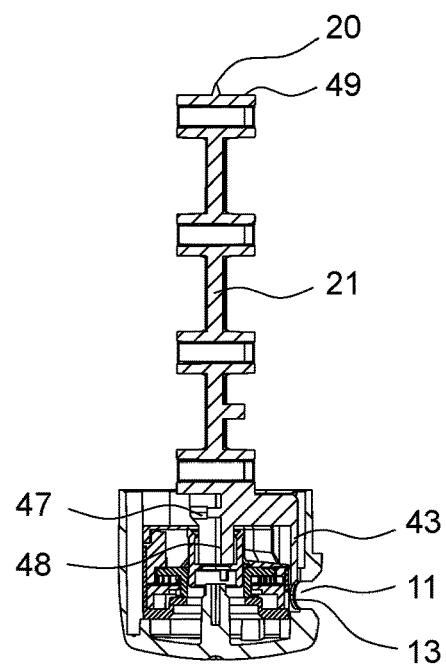
FIG. 11 shows a cross-section of the insert-base part according to FIG. 9.

With reference to the cross-sections in FIGS. 11 and 15, the pin 21 preferably has a shoulder 47, which rests on the dose indicator 12 in such a way that the dose indicator 12 can be actuated with the shoulder 47 when the pin 21 is moved toward the dose indicator or away from the dose indicator 12.

With further reference to the cross-sections in FIGS. 11 and 15, the pin 21 has a bolt 48 preferably on the end side, which slot is aligned or inserted into the dose indicator 12. With this bolt 48, the pin 21 can be adjusted relative to the dose indicator 12.

The pin 21 preferably has an actuating section 49 via which the pin 21 can be shifted axially. Preferably, upon actuation of the inhaler 1, in particular upon putting the inhaler 1 into the ready-to-trigger state by adding energy to the energy storage 19 and/or by tensioning the spring, the cartridge 18 or another part of the inhaler 1 comes into contact with the actuating section 49 and shifts the pin 21 and/or presses the pin 21 in the direction of the dose indicator 12. The dose indicator 12 can exert a restoring force on the pin 21 in order to subsequently move it back again in the opposite direction. As an alternative or in addition, another restoring means such as a restoring spring can be provided, which is produced separately from the dose indicator 12.

In this way, the pin 21 preferably executes a back-and-forth movement, in particular with each activation cycle. By this movement, the dose indicator 12 can be driven and/or the covering element 43 can be moved to form the readiness indicator 42. A stroke 50, which the pin 21 performs in its movement, is indicated with an arrow by way of example in FIGS. 8 and 9.

Figure 16:
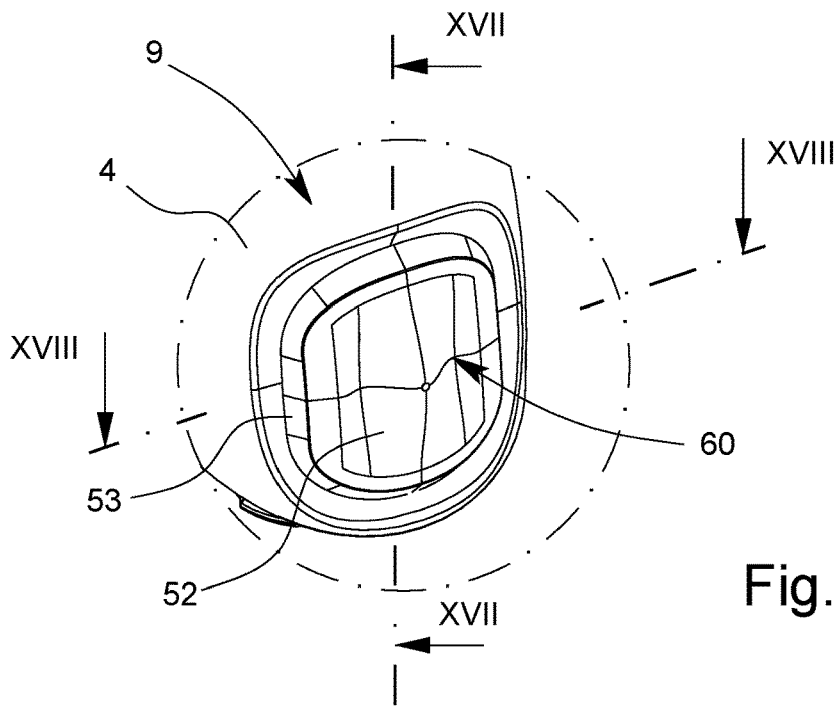
FIG. 16 shows a diagrammatic, perspective view of the breath indicator according to the invention.
Figure 17:
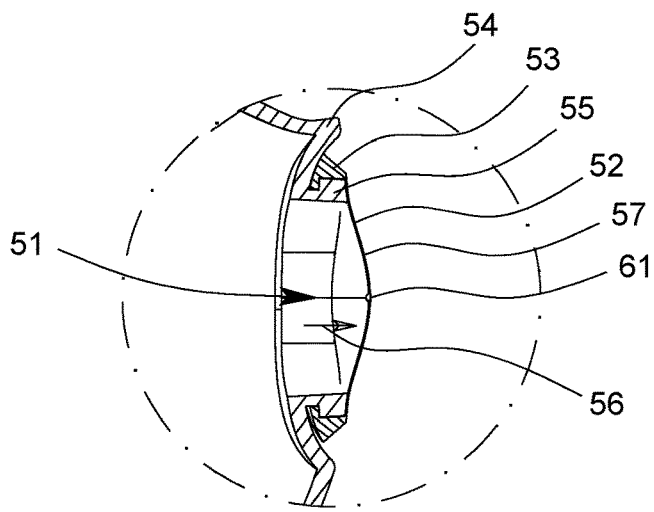
FIG. 17 shows a section of the breath indicator according to the invention along intersection line XVII-XVII of FIG. 16.
Figure 18:
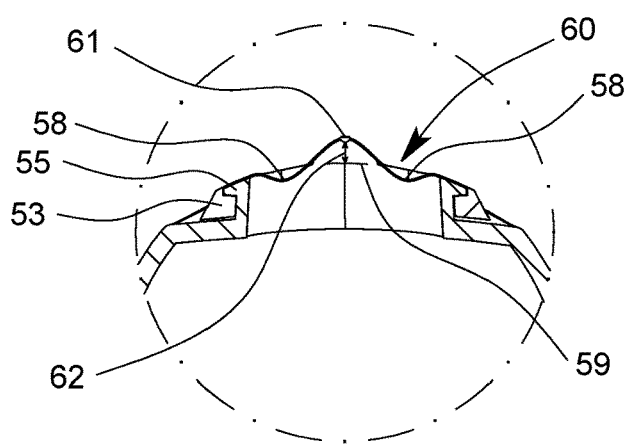
FIG. 18 shows a section of the breath indicator according to the invention along intersection line XVIII-XVIII of FIG. 16.

FIG. 16 depicts a top view of the breath indicator 9. FIGS. 17 and 18 show the breath indicator 9 in its installation situation as seen along lines XVII-XVII and XVIII-XVIII of FIG. 16, respectively.

The breath indicator 9 preferably closes an indicator opening 51 of the chamber 4. The indicator opening 51 communicates via the dispensing device 5 with the outlet 6. In this way, a respiratory action acts into the outlet 6 or out from the outlet 6 onto the breath indicator 9.

The breath indicator 9 has a membrane 52 which closes the indicator opening 51. The membrane 52 can be held by a membrane frame 53 of the indicator opening 51. To this end, the indicator opening 51 can have an opening frame 55 which corresponds to the membrane frame 53 or is formed in a complementary manner, by which the membrane 52 closes the indicator opening 51 in an airtight manner and is held or can be held at the chamber 4.

A respiratory action into the outlet 6 of the dispensing device 5 or out from the outlet 6 leads to a pressure differential 56 between the flat sides 57 of the membrane 52, caused by the outlet 6 communicating with the indicator opening 51.

The membrane 52 preferably has at least two half-waves 58 in cross-section, as depicted by way of example in FIG. 18. The half-waves 58 are curved inward relative to a reference line 59 in the illustrative example, but in principle can also be curved outward.

When the membrane 52 is provided with such half-waves 58, the visibility of a deformation that can be caused by the respiratory action can be improved.

This can be achieved, on the one hand, in that the membrane 52 is untensioned in the region of the half-waves 58, and a deformation and/or expansion of the membrane 52 therefore requires less force and/or pressure differential 56. On the other hand, the visibility of the deformation that can be caused by the respiratory action can be improved in that via the expansion of the membrane 52, the half-waves 58 experience a different deformation than other sections of the membrane 52, which results in more characteristic changes in the appearance of the membrane 52.

As an alternative or in addition, the membrane 52 is untensioned and/or relaxed at least in sections and/or in at least one direction. This advantageously results in an increased deflection relative to the same pressure differential 56 and thus to an improved visibility of the respiratory action.

The one or more half-waves 58 preferably form beads 60. As beads 60 in terms of the present invention, elongated inward or outward curves that occupy only a small or specific part of the membrane surface are understood, which curves promote movability of the membrane.

In the illustrative example, the beads 60 can be designed to be at least essentially parallel and not connected to one another. As an alternative, however, it is possible that the beads 60 can be designed to be connected to one another and/or circumferential along the membrane frame 53.

The membrane 52 preferably has at least one wave peak 61. In the illustrative example, the latter is provided in the center and/or symmetrical to the membrane frame 53. The wave peak 61, in particular when it is bounded by the half-waves 58, in a surprising way also improves the visibility of a respiratory action.

As a result, the half-waves 58 and/or a depressurized and/or wavy membrane 52, quite especially both in combination, lead in a surprising and advantageous way to an improved visualization of the respiratory action.

The breath indicator 9 can be formed as an integral piece, in particular injection-molded as an integral piece. Preferably, the membrane 52 is thus formed as an integral piece with the membrane frame 53. In this case, an injection point can be provided in the region of the wave peak 61. In the region of the injection point, the membrane 52 optionally is slightly thicker and/or stiffer due to production conditions and requires a higher pressure differential 56 for deformation in comparison to the membrane 52 apart therefrom, and in particular in comparison to the half-waves 58 or beads 60. Advantageously, however, the adjacent beads 60 lead to a movement of the wave peak 61 upon respiratory action even without deformation or in the case of only slight deformation of the wave peak 61. Thus, a readily recognizable visualization of the respiratory action is made possible even with a low pressure differential 56.

The wave peak 61 can have an amplitude 62, which is similar to or greater than the amplitude(s) of the adjacent half-waves 58 and/or beads 60. In this way, the wave peak 61 preferably projects slightly out of the alignment with the wall of the chamber 4 surrounding the indicator opening 51, which in turn improves the recognizability of a respiratory action even with a low pressure differential 56.

Quite especially preferred, therefore, is the combination of two half-waves 58 forming beads 60 with a wave peak 61 formed between the half-waves 58, since in this way, the described measures interact in a synergistic way and make possible an especially reliable display of the respiratory action.

Using FIGS. 19 to 27, an explanation is given below as to how the inhaler 1 according to the invention is advantageously put into a ready-to-use state by means of the insert.

In FIGS. 19 to 25, in each case a part of the inhaler 1 is depicted in a diagrammatic, simplified cross-section, in which the housing 2 is essentially masked for purposes of clarity.

Figure 19:
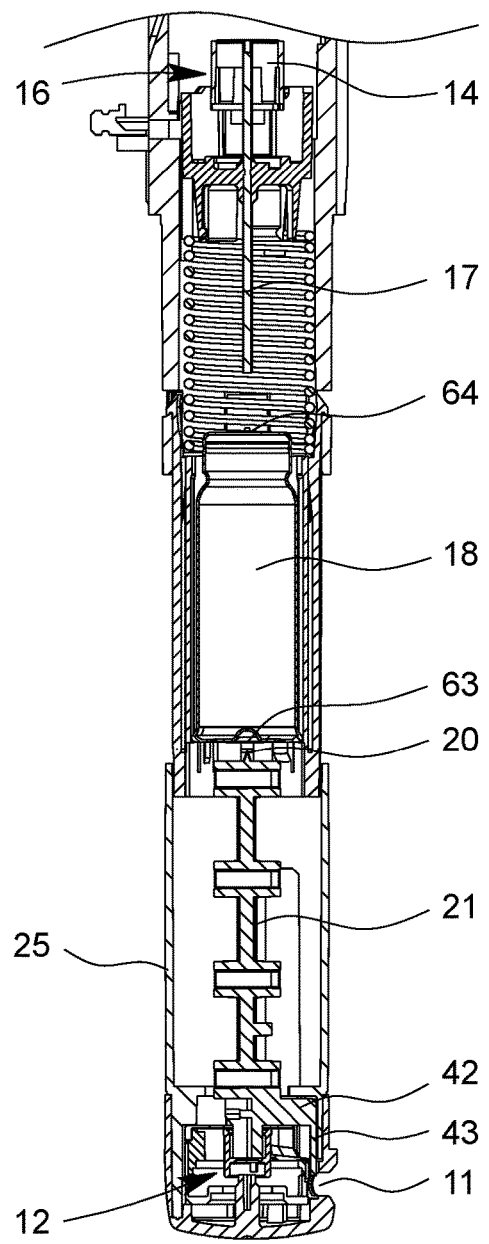
FIG. 19 shows a cross-sectional view of the inhaler according to the invention in a delivery state with the insert in a first position.

In the delivery state depicted in FIG. 19, the cartridge 18 is sealed. In particular, the cartridge 18 has an air hole seal 63, i.e., a seal that closes an air opening provided for pressure compensation. As an alternative or in addition, the cartridge 18 has a removal-opening seal 64, i.e., a seal that closes an opening of the cartridge 18 that is provided for the removal of the medication.

By moving the insert 25 into the housing 2, in particular into the housing-grip part 2B, the inhaler 1 can be put into a ready-to-use state.

The inhaler 1 is preferably put into the ready-to-use state only once or can be put into the ready-to-use state only once and/or irreversibly. A distinction should therefore be made in particular between the ready-to-use state and the ready-to-trigger state, since in terms of this invention, preferably both a ready-to-trigger state and a not-ready-to-trigger state (only then) are present when the inhaler 1 in principle is ready to use; the inhaler 1 thus has already been shifted into the ready-to-use state.

Using the cross-sections from FIGS. 20 to 23, an explanation is given below as to what effect the insertion of the insert 25 has or how the ready-to-use state is reached thereby.

Figure 20:
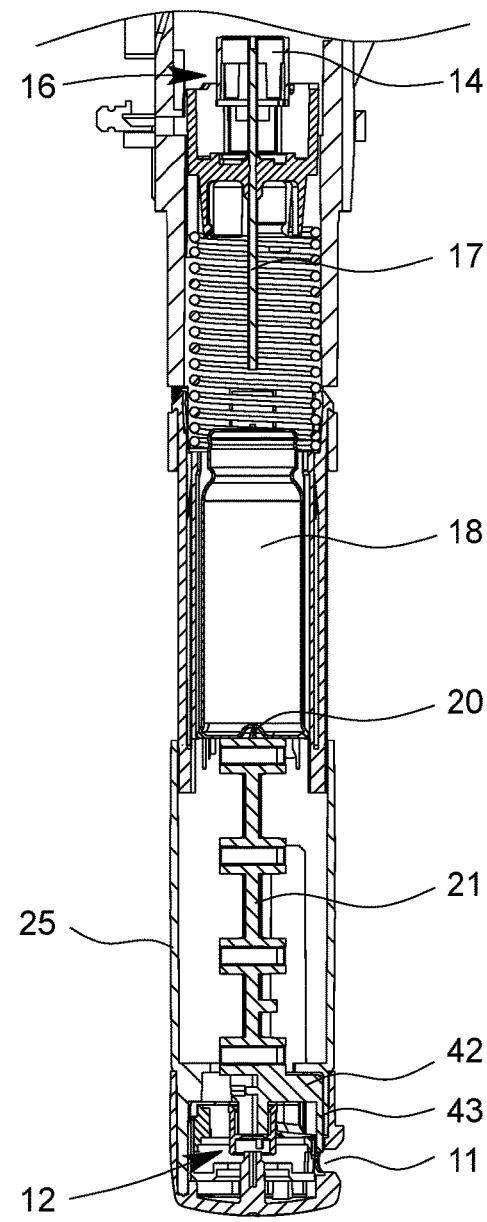
FIG. 20 shows a cross-sectional view of the inhaler according to the invention with the insert in a second position.

FIG. 20 depicts the state of the inhaler 1 when the insert 25 has been inserted slightly starting from the delivery state. Here, the tapping element 20 first punctures the air hole seal 63 and thus unblocks the aeration of the cartridge 18.

Subsequently, upon continued insertion of the insert 25, the cartridge 18 is pressed by the pin 21 in the direction of the discharge nozzle 14, i.e., in the direction of the pressure generator 16 and/or conveying pipe 17, and reaches the position depicted in FIG. 21, in which the insert 25 is inserted at least essentially into the housing 2. In this case, the cartridge 18 is connected first on the removal side by the conveying pipe 17. In order to do this, the conveying pipe 17 breaks through the removal-opening seal 64 and enters into the interior space of the cartridge 18. Thus, a fluidic connection of the interior space of the cartridge 18 with the pressure generator 16 and/or the discharge nozzle 14 is produced. Finally, the cartridge 18 reaches an end position in which it engages in a cartridge receptacle 65, in particular with a neck.

The cartridge receptacle 65 preferably fastens the conveying pipe 17 to the cartridge 18 and/or acts as a slide by which subsequently the cartridge 18 together with the conveying pipe 17 can be moved up and down, whereby the pressure generator 16 conveys the medication and nebulizes it by means of the discharge nozzle 14, which is shown still based on FIGS. 22 and 23. This movement of the cartridge receptacle 65 and thus of the cartridge 18 with tensioning of the spring is induced with the actuating lever 3. Also, triggering takes place preferably by an anew actuation of the actuating lever. For details in this connection, reference is made to the initially-mentioned publications.

Figure 23:
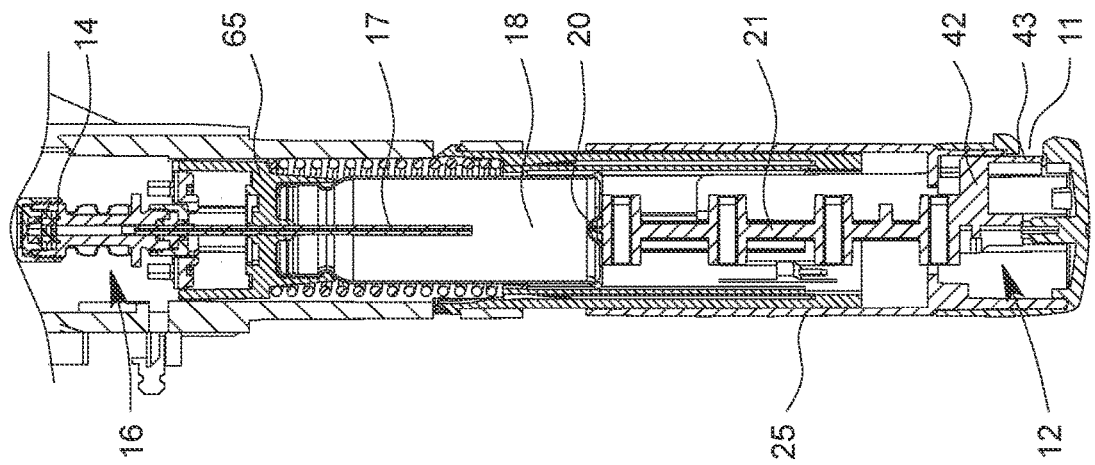
FIG. 23 shows a cross-sectional view of the inhaler according to the invention with the insert in a fifth position.
Figure 22:
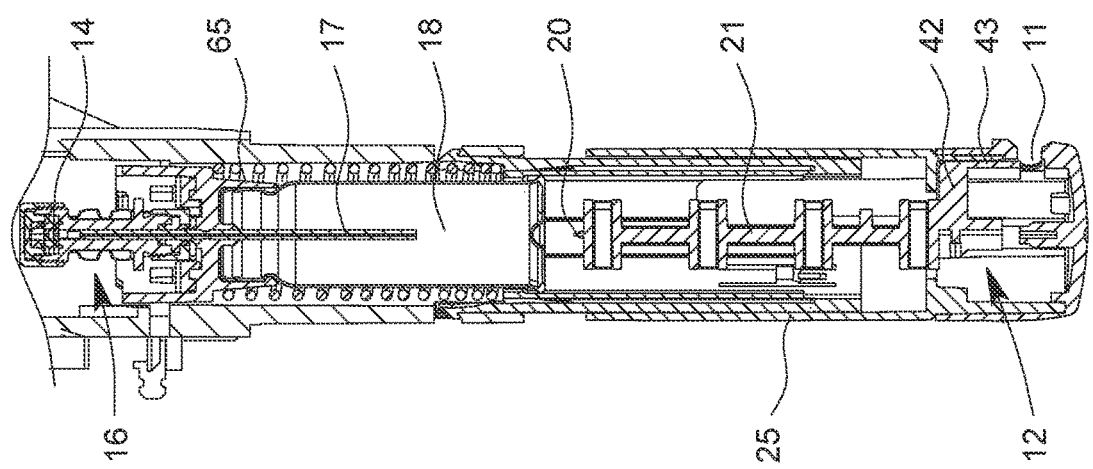
FIG. 22 shows a cross-sectional view of the inhaler according to the invention with the insert in a fourth position.

In cross-section, FIGS. 22 and 23 show the not-ready-to-trigger state and the ready-to-trigger state of the inhaler 1.

In the not-ready-to-trigger state of the inhaler 1, the energy storage 19 is unloaded and/or the spring, by which the energy storage 19 is created in the embodiment, is relaxed or only pretensioned. The cartridge 18 and/or the cartridge receptacle 65 is/are located at an uppermost position and/or at a position that is close to the discharge nozzle 14 and/or the pressure generator 16.

By putting the inhaler 1 into its ready-to-trigger state, which in the illustrative example can be done by actuating the actuating lever 3, the cartridge 18 together with the cartridge receptacle 65 is moved downward and/or away from the discharge nozzle 14 and/or the pressure generator 16. This brings about the loading of the energy storage 19, in the illustrative example by tensioning the spring and/or moving the pin 21, caused by the and in the same direction as the movement of the cartridge 18, by which preferably the dose indicator 12 is actuated and/or the covering element 43 of the readiness indicator 42 conceals the display 10 of the dose indicator 12, as depicted by way of example in FIG. 23.

Starting from this ready-to-trigger state, the inhaler 1 can be triggered preferably by another movement of the actuating lever 3, in particular in the same direction as upon putting the inhaler 1 into its ready-to-trigger state, namely preferably in the direction of the housing-grip part 2B. In doing so, a movement of the cartridge 18 together with the conveying pipe 17 in the direction of the pressure generator 16 and/or the discharge nozzle 14 is unblocked, whereby the medication is dispensed by means of the pressure generator 16, in particular is nebulized by the discharge nozzle 14. At the same time, the pin 21 moves at least partially with the cartridge 18, in such a way that the readiness indicator 42 displays the not-ready-to-trigger state, here by unblocking the view of the display 10 of the dose indicator 12. Subsequently, the inhaler 1 is located again in the not-ready-to-trigger state, depicted in FIG. 22.

Figure 21:
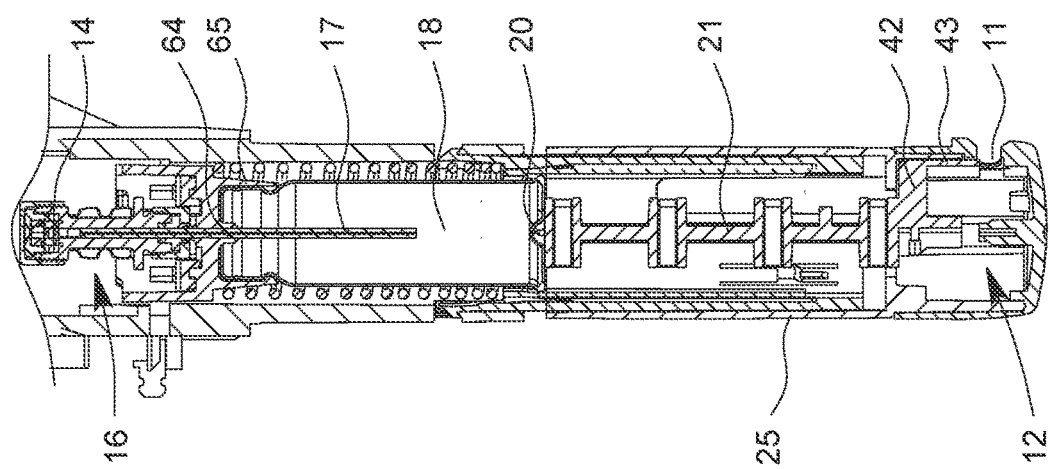
FIG. 21 shows a cross-sectional view of the inhaler according to the invention with the insert in a third position.
Figure 24:
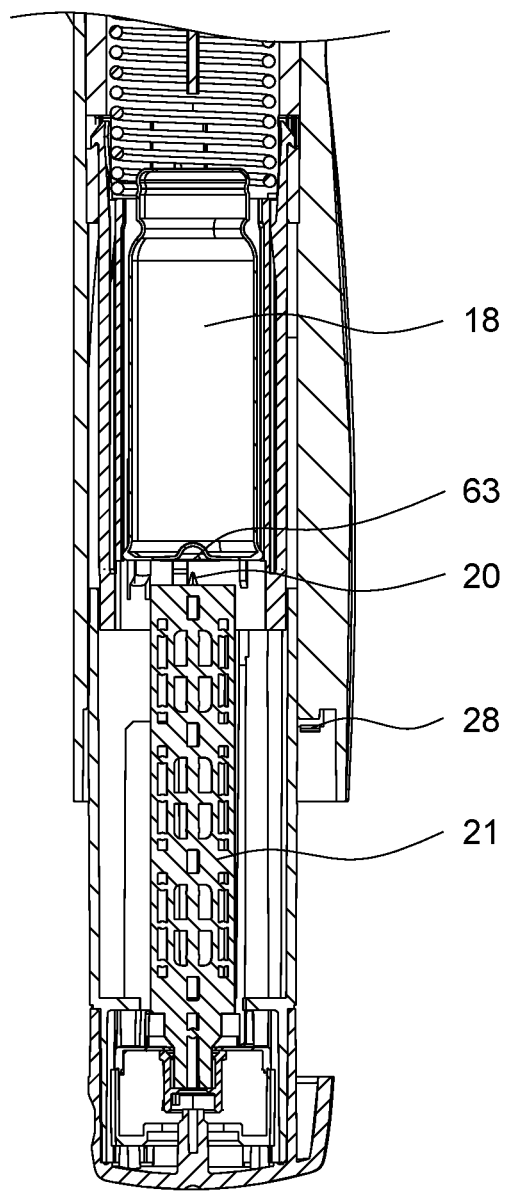
FIG. 24 shows a cross-sectional view of the inhaler according to the invention with an intact tamper-proof seal.
Figure 25:
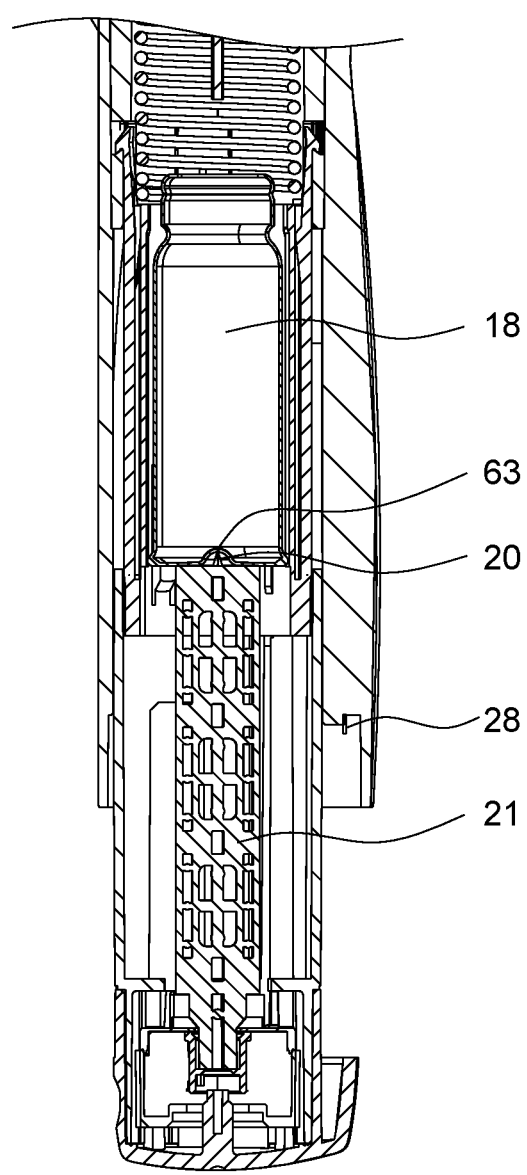
FIG. 25 shows a cross-sectional view of the inhaler according to the invention with a broken tamper-proof seal.

Corresponding to the state of FIG. 21, FIGS. 24 and 25 depict the initial phase of the insertion of the insert 25 for putting the inhaler 1 into the ready-to-use state in a different cross-sectional direction, such that the tamper-proof seal 28, which can also be seen in FIGS. 3 and 4, is broken starting from the position in FIG. 24 in the event that additional insertion is done, as depicted in FIG. 24.

The breaking of the tamper-proof seal 28 takes place in this case with or directly before the breaking of the air hole seal 63. Upon inserting the insert 25, the breaking of the tamper-proof seal 28 preferably produces a noticeable and/or (tactilely) traceable threshold that is to be overcome. Should the tamper-proof seal 28 be broken by accident already before the intended use of the inhaler 1, this can be detected during insertion by the fact that the threshold is missing. In this case, the inhaler 1 is to be discarded, since if a break in the tamper-proof seal 28 exists before use of the inhaler, the danger exists that the air hole seal 63 has also already been destroyed and its concentration or effectiveness can no longer be ensured because of possible discharge, in particular outgassing of components of the medication.

Figure 26:
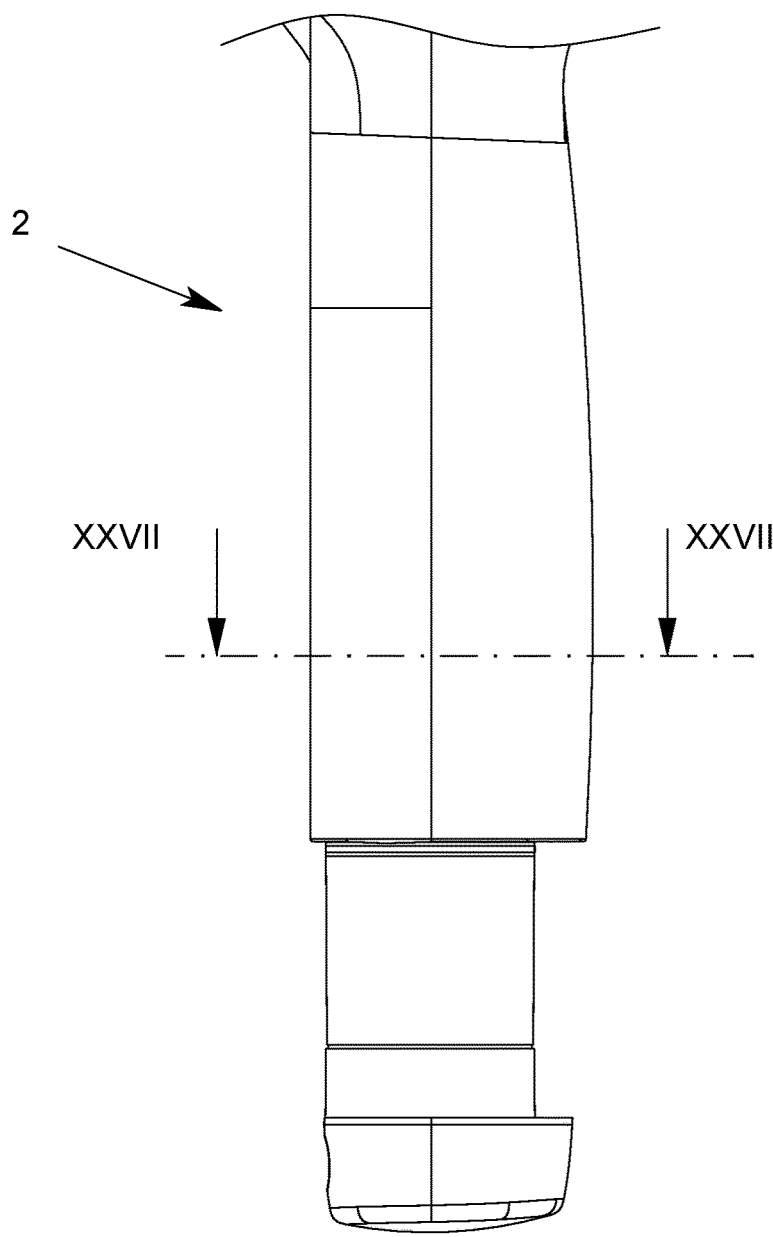
FIG. 26 shows a partial side view of the inhaler according to the invention with the insert in the first position.
Figure 27:
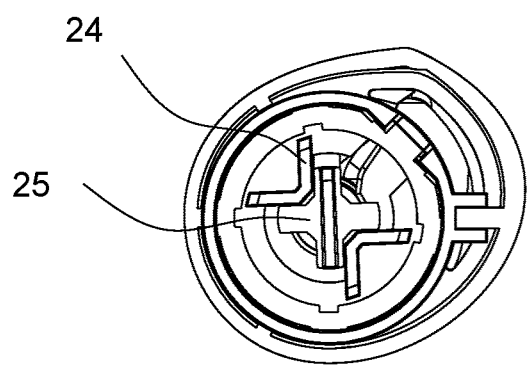
FIG. 27 shows a cross-sectional view of the inhaler according to the invention taken along line XXVII-XXVII of FIG. 26.

FIG. 26 in addition depicts a segmented side view of a part of the inhaler 1, and FIG. 27 depicts a section taken along line XXVII-XXVII in FIG. 26. Here, in addition, it can be seen that the pin 21 is made cross-shaped in cross-section, and the supporting device 24, corresponding thereto, is designed to engage in the pin 21 in such a way that the anti-rotational and straight-line guiding of the pin 21 is achieved.

The various aspects of this invention can be achieved both independently of one another and advantageously can be combined with one another.

What is claimed is:

1. Inhaler for dispensing a medication, comprising:
a housing,
a cartridge for the medication that is received in the housing, and
a protective device for protecting the inhaler against removal or replacement of the cartridge, the protective device damaging or causing damage in response to attempts to remove or replace the cartridge, whereby the inhaler becomes unusable for dispensing the medication without the protective device being repaired or replaced,
wherein the protective device has at least one fastening device which holds the cartridge in the inhaler or parts of the inhaler together, the fastening device being configured to be damaged when the inhaler is tampered with for the purpose of removing or replacing the cartridge, such that the inhaler is rendered unusable for the further administration of the medication due to the fastening device being no longer able to hold the cartridge in the inhaler or the parts of the inhaler together.

2. Inhaler according to claim 1, wherein the protective device is constructed so as to be damaged or destroyed when the cartridge is removed from the housing, such that the inhaler is rendered unusable for dispensing the medication without the protective device being repaired or replaced, and wherein the protective device holds at least one of the cartridge in the inhaler or parts of the inhaler together, such that the damaging or destroying of the protective device due to removing or replacing the cartridge terminates said holding of the cartridge in the inhaler or holding of the parts of the inhaler together.

3. Inhaler according to claim 1, wherein the at least one fastening device extends on a side facing away from the cartridge along a longitudinal axis of the protective device, so that a separating action on the housing in a region of the cartridge results in the damage by which the protective device is unable to hold at least one of the cartridge in the inhaler or the parts of the inhaler together.

4. Inhaler according to claim 1, wherein the at least one fastening device has an arm which carries a latching element for latching of the protective device, wherein by separating the arm or by damaging the latching element, the protective device is unable to hold the cartridge in the inhaler or the parts of the inhaler together.

5. Inhaler according to claim 1, wherein the at least one fastening device extends over a length that exceeds the length of the cartridge.

6. Inhaler according to claim 1, further comprising an insert which puts the inhaler in a ready-to-use state by insertion thereof, wherein for dispensing a medication, the insert is held by the protective device in an inserted position, wherein damaging of the protective device renders the protective device unable to hold the insert in the inserted position.

7. Inhaler according to claim 6, wherein the insert or a slide-in guide is formed of multiple parts which are connected together by the at least one fastening device, so that damage to the protective device enables the insert or slide-in guide to move in a manner rendering the inhaler unusable for dispensing of the medication.

8. Inhaler for dispensing a medication, comprising:
a housing,
a cartridge for the medication that is received in the housing, and
means for providing a not-ready-to-trigger state and a ready-to-trigger state,
wherein the inhaler has to be shifted from the not-ready-to-trigger state into the ready-to-trigger state in order to be subsequently triggerable, and
wherein the inhaler has a readiness indicator for at least one of displaying the ready-to-trigger state or the not-ready-to-trigger state,
wherein the inhaler comprises an energy storage for driving a mechanical pressure generator for delivering the medication, wherein the not-ready-to-trigger state is a state starting from which the inhaler must first be prepared by adding energy to the energy storage in order to be ready to trigger and wherein the energy storage is supplied with energy upon shifting the inhaler into the ready-to-trigger state, so that delivery of the medication can be effected, wherein the readiness indicator is adapted to provide an optical display upon shifting the inhaler into the ready-to-trigger state.

9. Inhaler according to claim 8, further comprising a dose indicator for displaying at least one of doses of the medication that have been dispensed or can still be dispensed or a fill level of a cartridge that has the medication, the readiness indicator being operated for at least partially concealing the dose indicator at least in one of the not-ready-to-trigger state or the ready-to-trigger state.

10. Inhaler according to claim 9, wherein the dose indicator is visible through a housing window of the inhaler wherein the readiness indicator is displayable through the same window, and wherein the readiness indicator at least partially conceals the dose indicator in one of the not-ready-to-trigger state and ready-to-trigger state and unblocks visibility of the dose indicator in the other of the not-ready-to-trigger state and ready-to-trigger state.

11. Inhaler according to claim 9, wherein the readiness indicator and the dose indicator share at least one of a housing window or a display.

12. Inhaler for dispensing a medication, further comprising an insert which, upon insertion of the insert into a housing of the inhaler, at least one of the following actions:
i) puts the inhaler into a ready-to-use state or
ii) automatically breaks a tamper-proof seal,
wherein the inhaler further comprises a cartridge receiving a medication that is to be dispensed, and wherein the cartridge is prepared for removal of the medication inside the housing by said insertion of the insert.

13. Inhaler according to claim 12, wherein the insert, in a delivery state of the inhaler, projects from the housing of the inhaler and is manually insertable at least partially further into the housing, and wherein the insert is manually insertable further into the housing to a latching position at which the insert engages irreversibly in an inserted position.

14. Inhaler according to claim 12, wherein the insert has one or both of a dose indicator, or a readiness indicator for displaying a trigger readiness.

15. Inhaler according to claim 12, wherein the insert has a dose indicator, wherein the insert has a pin on which at least one of the readiness indicator or an actuating section is provided for actuating the dose indicator, and wherein the pin is linearly movable in the insert and is secured against rotation.

16. Protective device for an inhaler having a cartridge for a medication that is received in a housing of the inhaler and wherein the protective device is adapted, in use, for protecting the inhaler against removal or replacement of the cartridge, so that the cartridge can be removed from the housing only by being damaged or destroyed, by which damage or destruction the inhaler is rendered unusable for administering the medication, wherein the protective device has at least one fastening device which has arms running along the protective device and on which latching elements are formed on an end thereof.

17. Protective device according to claim 16, further comprising a sleeve-like receptacle for the cartridge.

18. Protective device according to claim 17, further comprising a stop for limiting the movement of the cartridge, wherein the stop is formed in the receptacle, and the arms are fastened to the end of the receptacle on which the stop is provided, and on which the least one fastening device is connected to the receptacle.

19. A breath indicator for displaying a respiratory action when used with an inhaler,
wherein the breath indicator is connected in an airtight manner to an indicator opening of a chamber of the inhaler which communicates with a dispensing outlet of the inhaler,
wherein the breath indicator has a flexible membrane for displaying a pressure differential between opposite sides of the membrane generated by the respiratory action, and
wherein the membrane in one direction is at least one of untensioned, wavy or provided with two half-waves.

20. Breath indicator according to claim 19, wherein the membrane in cross-section has two beads that are formed by half-waves of the membrane.

21. Breath indicator according to claim 19, wherein the membrane in one direction is essentially at least one of unwaved, tensioned or curved.

22. Breath indicator according to claim 19, wherein the at least one wavy side has at least one of waves, half-waves or beads that have an amplitude of more than 0.5 mm in a region of the at least one of waves, half-waves or beads, or more than 10 times a material thickness of the membrane in a region of the at least one of waves, half-waves or beads.

23. Inhaler for dispensing a medication, comprising:
a housing,
a cartridge for the medication that is received in the housing,
a breath indicator for displaying a respiratory action with the inhaler, wherein the breath indicator is connected in an airtight manner to an indicator opening of a chamber of the inhaler which communicates with an outlet of the inhaler, wherein the breath indicator has a flexible membrane for displaying a pressure differential between opposite sides of the membrane generated by the respiratory action, and wherein the membrane is wavy on at least one side thereof.

* * * * *